United States Patent
Burns et al.

(10) Patent No.: US 9,205,205 B2
(45) Date of Patent: *Dec. 8, 2015

(54) SINGLE-USE AUTO-DISABLE SYRINGE

(75) Inventors: Steven Burns, Monroe, NY (US); Russell Cole, New York, NY (US); Chee L. Lum, Pequannock, NJ (US); David Martinez Llanos, Madrid (ES); Michael Soltz, Springfield, NJ (US); Ramon Arazo Urraca, Fraga (Huesca) (ES); Luis Saldana, Fraga (Huesca) (ES)

(73) Assignee: Becton, Dickinson and Company, Franklin Lakes, NJ (US)

( * ) Notice: Subject to any disclaimer, the term of this patent is extended or adjusted under 35 U.S.C. 154(b) by 401 days.

This patent is subject to a terminal disclaimer.

(21) Appl. No.: 13/619,860

(22) Filed: Sep. 14, 2012

(65) Prior Publication Data
US 2013/0110076 A1  May 2, 2013

Related U.S. Application Data

(63) Continuation of application No. 12/591,660, filed on Nov. 25, 2009, now Pat. No. 8,287,491.

(60) Provisional application No. 61/118,411, filed on Nov. 26, 2008, provisional application No. 61/202,318, filed on Feb. 18, 2009, provisional application No. 61/202,837, filed on Apr. 9, 2009.

(51) Int. Cl.
*A61M 5/50* (2006.01)
*A61M 5/32* (2006.01)
*A61M 5/31* (2006.01)

(52) U.S. Cl.
CPC ............. *A61M 5/502* (2013.01); *A61M 5/3202* (2013.01); *A61M 5/3213* (2013.01);

(Continued)

(58) Field of Classification Search
CPC . A61M 5/3202; A61M 5/3213; A61M 5/502; A61M 5/3146; A61M 2005/5033; A61M 2005/581; A61M 2005/582; A61M 2005/5026
USPC .................. 604/110, 181, 187, 218, 220, 221
See application file for complete search history.

(56) References Cited

U.S. PATENT DOCUMENTS 3,478,937 A   11/1969  Solowey
3,563,240 A    2/1971  Silver
(Continued)

FOREIGN PATENT DOCUMENTS

AU          641123      11/1989
AU          677574       5/1997
(Continued)

OTHER PUBLICATIONS

Becton, Dickinson and Company, "BD SoloShot™ LX—BCG Auto-Disable Syringe—Reducing the Risk of Needle Reuse," Brochure BD 7/03 7017-Rev1, 2003, USA.
(Continued)

*Primary Examiner* — Laura Bouchelle
(74) *Attorney, Agent, or Firm* — Dickinson Wright PLLC

(57) ABSTRACT

A single-use auto-disable syringe device utilizes a locking element to prevent re-use of the syringe by locking the plunger rod with respect to the barrel upon completion of an injection stroke. The plunger rod includes a plurality of teeth comprising distally facing shoulders provided on a majority of the length of an elongate portion of the plunger rod.

30 Claims, 20 Drawing Sheets

(52) U.S. Cl.
CPC ..... *A61M 5/3146* (2013.01); *A61M 2005/5026* (2013.01); *A61M 2005/5033* (2013.01); *A61M 2205/581* (2013.01); *A61M 2205/582* (2013.01); *Y10T 29/49268* (2015.01)

(56) References Cited

U.S. PATENT DOCUMENTS

| | | | |
|---|---|---|---|
| 3,747,812 A | 7/1973 | Karman et al. | |
| 3,934,586 A | 1/1976 | Easton et al. | |
| 3,951,146 A | 4/1976 | Chiquiar-Arias | |
| 4,212,309 A | 7/1980 | Moorehead | |
| 4,244,366 A | 1/1981 | Raines | |
| 4,246,898 A | 1/1981 | Travalent et al. | |
| 4,252,118 A | 2/1981 | Richard et al. | |
| 4,267,846 A | 5/1981 | Kontos | |
| 4,367,738 A | 1/1983 | Legendre et al. | |
| 4,373,526 A | 2/1983 | Kling | |
| 4,424,817 A | 1/1984 | Williams | |
| 4,563,178 A | 1/1986 | Santeramo | |
| 4,642,102 A | 2/1987 | Ohmori | |
| 4,699,614 A | 10/1987 | Glazier | |
| 4,711,637 A | 12/1987 | Leigh et al. | |
| 4,731,068 A | 3/1988 | Hesse | |
| 4,775,363 A | 10/1988 | Sandsdalen | |
| 4,775,364 A | 10/1988 | Alles | |
| 4,820,272 A | 4/1989 | Palmer | |
| 4,826,483 A | 5/1989 | Molnar | |
| 4,863,427 A | 9/1989 | Cocchi | |
| 4,883,466 A | 11/1989 | Glazier | |
| 4,883,473 A | 11/1989 | Thomas | |
| 4,887,999 A | 12/1989 | Alles | |
| 4,915,692 A | 4/1990 | Verlier | |
| 4,919,652 A | 4/1990 | Alter et al. | |
| 4,923,443 A | 5/1990 | Greenwood et al. | |
| 4,950,163 A | 8/1990 | Zimble | |
| 4,950,240 A | 8/1990 | Greenwood et al. | |
| 4,961,728 A | 10/1990 | Kosinski | |
| 4,973,308 A | 11/1990 | Borras et al. | |
| 4,973,310 A | 11/1990 | Kosinski | |
| 4,978,339 A | 12/1990 | Labouze et al. | |
| 4,986,812 A | 1/1991 | Perler | |
| 4,990,141 A | 2/1991 | Byrne et al. | |
| 4,995,871 A | 2/1991 | Sasaki et al. | |
| 5,000,737 A | 3/1991 | Free et al. | |
| 5,004,460 A | 4/1991 | Gimeno | |
| 5,019,045 A | 5/1991 | Lee | |
| 5,021,047 A | 6/1991 | Movern | |
| 5,037,393 A | 8/1991 | Ellgass | |
| 5,047,017 A | 9/1991 | Koska | |
| 5,059,181 A | 10/1991 | Agran | |
| 5,062,833 A | 11/1991 | Perler | |
| 5,067,942 A | 11/1991 | Jaffe et al. | |
| 5,078,686 A | 1/1992 | Bates | |
| 5,085,638 A | 2/1992 | Farbstein et al. | |
| 5,085,640 A | 2/1992 | Gibbs | |
| 5,090,962 A | 2/1992 | Landry et al. | |
| 5,095,914 A | 3/1992 | Sarstedt | |
| 5,098,402 A | 3/1992 | Davis | |
| 5,106,372 A | 4/1992 | Ranford | |
| 5,112,318 A | 5/1992 | Novacek et al. | |
| 5,127,906 A | 7/1992 | Landry et al. | |
| 5,149,323 A | 9/1992 | Colonna | |
| 5,163,918 A | 11/1992 | Righi et al. | |
| 5,181,912 A | 1/1993 | Hammett | |
| 5,183,466 A | 2/1993 | Movern | |
| 5,205,825 A | 4/1993 | Allison et al. | |
| 5,215,524 A | 6/1993 | Vallelunga et al. | |
| 5,215,536 A | 6/1993 | Lampropoulos et al. | |
| 5,222,942 A | 6/1993 | Bader | |
| 5,222,948 A | 6/1993 | Austin et al. | |
| 5,226,882 A | 7/1993 | Bates | |
| 5,250,030 A | 10/1993 | Corsich | |
| 5,257,976 A | 11/1993 | Fenet | |
| 5,290,235 A | 3/1994 | Polyblank et al. | |
| 5,308,328 A | 5/1994 | Gonzalez | |
| 5,318,537 A | 6/1994 | Van Der Merwe | |
| 5,334,156 A | 8/1994 | Gonzalez | |
| 5,352,203 A | 10/1994 | Vallelunga et al. | |
| 5,370,620 A | 12/1994 | Shonfeld | |
| 5,380,295 A | 1/1995 | Vacca | |
| 5,423,756 A | 6/1995 | Van Der Merwe | |
| 5,478,321 A | 12/1995 | Kimber | |
| 5,527,285 A | 6/1996 | Lenz et al. | |
| 5,527,286 A | 6/1996 | Lekhgolts et al. | |
| 5,531,691 A | 7/1996 | Shonfeld et al. | |
| 5,540,666 A | 7/1996 | Barta et al. | |
| 5,558,637 A | 9/1996 | Allonen et al. | |
| 5,562,623 A | 10/1996 | Shonfeld et al. | |
| 5,593,387 A | 1/1997 | Rupp | |
| 5,624,406 A | 4/1997 | Labouze | |
| 5,643,211 A | 7/1997 | Sadowski et al. | |
| 5,738,655 A | 4/1998 | Vallelunga et al. | |
| 5,814,017 A | 9/1998 | Kashmer | |
| 5,820,605 A | 10/1998 | Zdeb et al. | |
| 5,833,660 A | 11/1998 | Nathan et al. | |
| 5,928,202 A | 7/1999 | Linnebjerg | |
| 5,989,219 A | 11/1999 | Villas et al. | |
| 5,989,220 A | 11/1999 | Shaw et al. | |
| 6,013,056 A | 1/2000 | Pettersen et al. | |
| 6,120,479 A | 9/2000 | Campbell et al. | |
| 6,139,526 A | 10/2000 | Bedner et al. | |
| 6,196,997 B1 | 3/2001 | Saito | |
| 6,210,371 B1 | 4/2001 | Shaw | |
| 6,217,550 B1 | 4/2001 | Capes | |
| 6,221,055 B1 | 4/2001 | Shaw et al. | |
| 6,267,749 B1 | 7/2001 | Miklos et al. | |
| 6,283,941 B1 | 9/2001 | Schoenfeld et al. | |
| 6,368,306 B1 | 4/2002 | Koska | |
| 6,423,033 B1 | 7/2002 | Tsai | |
| 6,533,756 B2 | 3/2003 | Schoenfeld et al. | |
| 6,579,269 B1 | 6/2003 | Kleyman | |
| 6,599,269 B1* | 7/2003 | Lewandowski et al. | 604/110 |
| 6,607,507 B2 | 8/2003 | Schottli | |
| 6,645,179 B1 | 11/2003 | Ishikawa et al. | |
| 6,719,722 B1 | 4/2004 | Yang | |
| 6,790,197 B2 | 9/2004 | Kosinski et al. | |
| 6,872,193 B2 | 3/2005 | Shaw et al. | |
| 6,991,618 B2 | 1/2006 | Lau et al. | |
| 7,052,482 B2 | 5/2006 | Lau et al. | |
| 7,141,039 B2 | 11/2006 | Tsai | |
| 7,282,042 B2 | 10/2007 | Wang | |
| 7,303,546 B2 | 12/2007 | Cirac Sole et al. | |
| 7,387,615 B2 | 6/2008 | Coelho et al. | |
| 7,460,085 B2 | 12/2008 | Ishii | |
| 7,500,967 B2 | 3/2009 | Thorley et al. | |
| 7,588,556 B2 | 9/2009 | Byrne et al. | |
| 7,704,426 B2 | 4/2010 | Earhart et al. | |
| 7,740,610 B2 | 6/2010 | Moh et al. | |
| 7,798,993 B2 | 9/2010 | Lim et al. | |
| 7,806,860 B2 | 10/2010 | Walton et al. | |
| 7,824,380 B2 | 11/2010 | Iijima et al. | |
| 7,908,100 B2 | 3/2011 | Kawabe | |
| 8,052,654 B2 | 11/2011 | Kaal et al. | |
| 8,287,491 B2* | 10/2012 | Burns et al. | 604/110 |
| 2002/0165500 A1 | 11/2002 | Bechtold et al. | |
| 2003/0073959 A1 | 4/2003 | Koska | |
| 2004/0039334 A1 | 2/2004 | Li | |
| 2004/0059294 A1 | 3/2004 | Pelkey et al. | |
| 2005/0033228 A1 | 2/2005 | Wang | |
| 2005/0038393 A1 | 2/2005 | Doyle et al. | |
| 2005/0038394 A1 | 2/2005 | Schwarzbich | |
| 2005/0187518 A1 | 8/2005 | Pelkey et al. | |
| 2005/0261635 A1 | 11/2005 | Byrne et al. | |
| 2006/0079839 A1 | 4/2006 | Moh et al. | |
| 2006/0161104 A1 | 7/2006 | Canadas Serrano | |
| 2006/0264824 A1 | 11/2006 | Swisher | |
| 2007/0043322 A1 | 2/2007 | Lee et al. | |
| 2007/0060885 A1 | 3/2007 | Wu | |
| 2007/0299395 A1 | 12/2007 | Pelkey et al. | |
| 2008/0021391 A1 | 1/2008 | Polidoro et al. | |
| 2008/0083041 A1 | 4/2008 | Santini et al. | |
| 2008/0097305 A1 | 4/2008 | Tsai | |
| 2008/0097307 A1 | 4/2008 | Walton et al. | |
| 2008/0154212 A1 | 6/2008 | Schraga | |

(56) References Cited

U.S. PATENT DOCUMENTS

| | | |
|---|---|---|
| 2008/0171969 A1 | 7/2008 | Byrne et al. |
| 2008/0188807 A1 | 8/2008 | Caizza et al. |
| 2008/0208119 A1 | 8/2008 | Walton et al. |
| 2009/0018503 A1 | 1/2009 | Walton et al. |
| 2009/0024094 A1 | 1/2009 | Eichhorst et al. |
| 2009/0171287 A1 | 7/2009 | Walton et al. |

FOREIGN PATENT DOCUMENTS

| | | |
|---|---|---|
| AU | 733649 | 5/2001 |
| CN | 16494742 A | 8/2005 |
| CN | 1694743 A | 11/2005 |
| DE | 3828127 | 2/1990 |
| DE | 202004018738 | 3/2005 |
| EP | 0037920 | 10/1981 |
| EP | 0360329 | 3/1990 |
| EP | 0409134 | 2/1994 |
| EP | 0643977 | 3/1995 |
| EP | 0646384 | 7/1995 |
| EP | 0489750 | 4/1996 |
| EP | 1123713 B1 | 6/2004 |
| EP | 1260343 | 9/2004 |
| EP | 1551483 | 1/2007 |
| EP | 1486225 | 2/2007 |
| EP | 1935444 | 6/2008 |
| EP | 1514566 | 8/2008 |
| ES | 1006813 | 1/1989 |
| ES | 2008949 | 8/1989 |
| ES | 1015155 | 6/1991 |
| ES | 1023361 | 7/1993 |
| ES | 1032723 | 6/1996 |
| FR | 1186571 A | 8/1959 |
| FR | 2639832 | 6/1990 |
| FR | 2707503 | 1/1995 |
| GB | 2184657 | 7/1987 |
| GB | 2202747 | 10/1988 |
| GB | 2234175 | 1/1991 |
| GB | 2246297 | 1/1992 |
| GB | 2315414 | 2/1998 |
| GB | 2414939 | 12/2005 |
| GB | 2416698 | 2/2006 |
| GB | 2420713 | 12/2007 |
| JP | 59016647 U | 2/1984 |
| JP | H11342200 A | 12/1999 |
| JP | 2001187141 A | 7/2001 |
| JP | 2003505161 A | 2/2003 |
| JP | 2004188148 | 7/2004 |
| JP | 2006500172 A | 1/2006 |
| JP | 2006500174 A | 1/2006 |
| WO | WO8909631 | 10/1989 |
| WO | WO8910150 | 11/1989 |
| WO | WO8910151 | 11/1989 |
| WO | WO9003818 | 4/1990 |
| WO | WO9116096 | 10/1991 |
| WO | WO9217223 | 10/1992 |
| WO | WO9412229 | 6/1994 |
| WO | WO9944661 | 9/1999 |
| WO | WO0038769 | 7/2000 |
| WO | WO0107106 | 2/2001 |
| WO | WO0164272 | 9/2001 |
| WO | WO0180932 | 11/2001 |
| WO | WO2004080513 | 9/2004 |
| WO | WO2005058398 | 6/2005 |
| WO | WO2006029448 | 3/2006 |
| WO | WO2006119667 | 11/2006 |
| WO | WO2007019164 | 2/2007 |
| WO | WO2007045901 | 4/2007 |

OTHER PUBLICATIONS

*Becton, Dickinson and Company*, "Introducing the New BD SoloShot™ IX—Auto-Disable Syringe with Colour-Coded Plunger—Everyone Deserves the Chance to Grow Up," Brochure BD 7/03 0156.Rev2a, 2003.

*Becton, Dickinson and Company*, "BD SoloShot™ IX—Auto-Disable Syringe—Instructions for Use," Brochure Bd 07/04 BDI 1003-E Rev.3, 2004.

\* cited by examiner

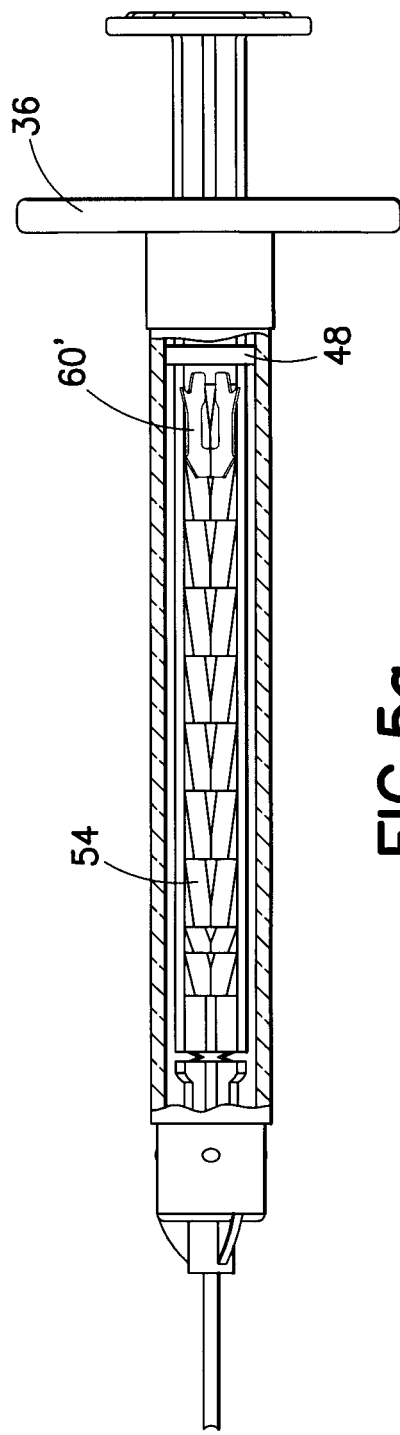
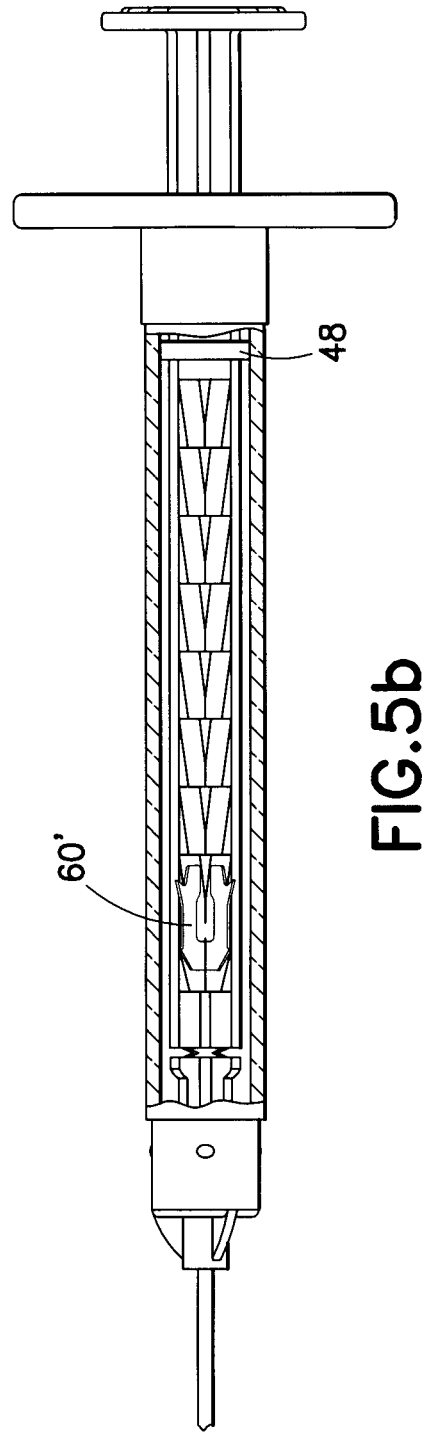
FIG.5a
FIG.5b

SINGLE-USE AUTO-DISABLE SYRINGE

RELATED APPLICATIONS

This application is a continuation of U.S. patent application Ser. No. 12/591,660, which is hereby incorporated in its entirety, and which was filed on Nov. 25, 2009 now U.S. Pat. No. 6,287,491 and claims the benefit of U.S. Provisional Patent Application Ser. No. 61/118,411, filed on Nov. 26, 2008, Ser. No. 61/202,318, filed on Feb. 18, 2009, and Ser. No. 61/202,837, filed on Apr. 9, 2009, each of which is hereby incorporated in its entirety.

FIELD OF THE INVENTION

The invention relates to a single-use syringe that employs a locking device for locking the plunger rod assembly of the syringe as well as a frangible feature on the plunger rod assembly to prevent re-use of the syringe, and that can be provided in a reduced size to reduce manufacturing costs.

BACKGROUND OF THE INVENTION

In the United States and throughout the world, the re-use of hypodermic syringe products that are intended for single use only is instrumental in drug abuse and more particularly, in the transfer of diseases. Intravenous drug users who routinely share and reuse syringes are a high risk group with respect to the AIDS virus. Also, the effects of re-use are a major concern in developing countries where repeated use of syringe products may be responsible for the spread of many diseases.

Many syringes have been designed to remedy this problem. Some of these have required a specific act to destroy the syringe after use either by using a destructive device or by providing the syringe assembly with frangible zones so that the syringe can be rendered inoperable by the application of force. These syringes allow the destruction or defeating of the syringe function through a conscious act by the syringe user. Although many of these devices work quite well, they do require the specific intent of the user followed by the actual act to destroy or render the syringe inoperable. None of these devices is effective with a user having the specific intent to re-use the hypodermic syringe.

Single-use hypodermic syringes that become inoperative or incapable of further use automatically without any additional act on the part of the user have been developed. One such syringe is disclosed in commonly-assigned U.S. Pat. No. 4,961,728, which is hereby incorporated by reference. The syringe disclosed in this patent includes a locking element positioned in the syringe barrel. The locking element includes proximally and outwardly facing barbs that engage the inner surface of the syringe barrel and an inwardly facing driving edge adapted to interact with a plunger rod to move the locking element along the barrel as the plunger rod is advanced during injection. A stopper is provided at the distal end of the plunger rod and is in a slidable, fluid tight engagement with the syringe barrel. The plunger rod includes a ledge positioned at a distance from the proximal side of a support wall that approximates the length of the locking element. The driving edge of the locking element engages the ledge, thereby ensuring that the locking element moves distally with the plunger rod and stopper. Other syringes including similar locking elements and functionality are disclosed in commonly-assigned U.S. Pat. Nos. 5,989,219 and 6,790,197, which are also incorporated herein by reference.

U.S. Pat. Nos. 5,021,047, 5,062,833 and 5,562,623 disclose single-use syringes having plunger rods that have teeth or ridges and locking elements that engage the teeth or ridges. The locking elements of these syringes also include outwardly extending teeth or prongs that engage the inside surface of the syringe barrel. The plunger rods of these syringes can be retracted to draw fluid into the syringe barrel while the locking elements remain stationary. Distal movement of the plunger rods causes the fluid to be expelled, while the locking elements move distally with the plunger rods with the intention of preventing further plunger rod retraction.

Although the prior art provides syringes having locking elements that will automatically lock the plunger rod to help prevent re-use, the use of such syringes has not been adopted on as large of a scale as necessary, especially in afflicted communities with diminished resources or impoverished nations, to satisfactorily aid in the prevention of drug abuse and the spread of disease. The cost of implementing such a product is a driving force in the adoption of such syringes in developing countries and communities or facilities where drug abuse and diseases are prevalent. Further, because of the typical costs associated with existing syringes one is enticed to attempt the re-use of such a device. Accordingly, there is a desire to produce such a syringe that is more cost effective, thus discouraging its attempted re-use and facilitating more widespread use. It is also desirable to produce such a cost effective single-use syringe that is both optimally effective in preventing its re-use and is easy to use. Namely, it is desirable to reduce the cost of materials and manufacture as well as other associated costs without compromising the effectiveness of the syringe. The smaller sized syringe enabled by the present invention is advantageous in providing a syringe that is more cost effective, thus enabling its widespread use in developing countries and communities where re-use of syringe products may be responsible for the spread of many diseases.

A single use syringe in accordance with embodiments of the present invention is ideal for use in facilities or communities participating in immunization programs to stop the spread of disease. The need for a smaller, yet functional device is further driven by the typical size of an immunization dosage. Such immunization and other similar dosage amounts are often very small, and the use of a smaller device results in many benefits, such as less waste of dosage contents, and ease of use in correctly setting smaller doses because of a heightened perception of the set dosage. Still further, as the typical usage of such devices is with young children or infants, a smaller, yet effective functional device, helps to relieve patient anxiety upon seeing the device. A smaller device avoids the levels of patient anxiety associated with seeing a larger device, especially with pediatric patients.

Providing such a device with the advantages discussed above is not without its challenges. For instance, a balance needs to be achieved between the strength and rigidity of syringe components, namely the plunger rod assembly and locking device, that will provide the optimal effectiveness without compromising the ease of use for the user or the desired functionality of the syringe. Maintaining effective functionality with the reduction in size that is possible with the present syringe device introduces a need for additional features not found in the prior art. A frangible feature is desired along the plunger rod that will cause the destruction of the syringe's functionality if an attempt is made to misuse or re-use the syringe. With a reduced size of the plunger rod assembly, known methods of providing such a frangible feature would unsatisfactorily result in a weakened plunger rod susceptible to inadvertent failure. The frangible feature should be provided in a manner that limits the possibility of accidental destruction of the plunger rod assembly during normal use. In particular, the functionality of the used syringe should be destroyed only upon applying excessive rotational or axial force to the syringe plunger in an attempt to disable the plunger locking mechanism and re-use the syringe. Further, because of the overall reduced size of the syringe, the construction of known plunger rod assemblies would result in a syringe unable to administer the plurality of dosage sizes required by vaccinations and other applications, while effectively preventing its re-use.

Therefore, there is a need for providing more cost effective single-use syringes that are still capable of providing a desired functionality during normal use, while effectively preventing their misuse or re-use.

SUMMARY OF THE INVENTION

Exemplary embodiments of the present invention address at least the above problems and/or disadvantages and provide at least the advantages described below. The invention relates to a syringe assembly which can be reduced in size and which includes a locking element capable of locking a plunger rod with respect to a syringe barrel and a frangible feature on the plunger rod to prevent intentional misuse or re-use of the syringe. The frangible feature is advantageously provided along the plunger rod in specific relation to the positioning of the locking device within the syringe barrel, such that the locking device supports the plunger rod from inadvertent failure during normal use of the device, yet enables destruction of the device upon attempted re-use.

In one exemplary embodiment, a syringe assembly comprises a syringe barrel having an inside surface defining a chamber, an open end, and a distal end. The syringe assembly further comprises a plunger rod assembly including an elongate body portion, a recess along the elongate body portion and a stopper connected to the elongate body portion. The elongate body portion further includes a portion of reduced cross-sectional area configured to break upon the application of excessive axial or torsional force to the plunger rod assembly. A locking element is slidably positioned within the chamber, and engages the inner surface of the syringe barrel such that the locking element is substantially immovable in the direction of the open end of the syringe barrel. The locking element is also engageable with the plunger rod assembly such that the plunger rod assembly and locking element are movable distally together toward the distal end of the syringe barrel. The locking element preferably includes a body portion having a proximal end that engages the plunger rod assembly or the inner surface of the syringe barrel at a surface more proximal than the reduced cross-sectional area of the plunger rod assembly. Additionally, the plunger rod assembly further comprises a plurality of first teeth formed on the elongate body portion, the first teeth defining a plurality of distally facing shoulders, which are substantially equally spaced along the elongate body portion. The plunger rod assembly of this embodiment further comprises a second tooth formed on the elongate body portion defining an intermediate distally facing shoulder provided between a first and second distally facing shoulder. The first and second distally facing shoulders are preferably positioned most distally on the elongate body portion among the plurality of distally facing shoulders. The reduced cross-sectional area of the plunger rod is provided near a distal end of the elongate body portion of the plunger rod assembly. The distal end of the elongate body portion is defined as the portion extending proximally from the stopper to the first distally facing shoulder. In this exemplary embodiment, after injection of a set dose, the locking element engages the plunger rod assembly or the inner surface of the syringe barrel along the distal end of the elongate body portion.

In another exemplary embodiment, a syringe assembly comprises a syringe barrel having an inside surface defining a chamber, an open end, and a distal end. The syringe assembly further comprises a plunger rod assembly including an elongate body portion, a recess along the elongate body portion and a stopper connected to the elongate body portion. The elongate body portion further includes a portion of reduced cross-sectional area configured to break upon the application of excessive axial or torsional force to the plunger rod assembly. The reduced cross-sectional area of the plunger rod is preferably provided near a distal end of the elongate body portion of the plunger rod assembly. The distal end comprises a portion extending proximally from the stopper to a first distally facing shoulder defined by a first tooth of a plurality of first teeth formed on the elongate body portion. The present exemplary embodiment includes a locking element slidably positioned within the chamber. The locking element engages the inner surface of the syringe barrel such that the locking element is substantially immovable in the direction of the open end of the syringe barrel. The locking element further engages the plunger rod assembly such that the plunger rod assembly and the locking element are movable distally together toward the distal end of the syringe barrel. The locking element includes a body portion having a proximal end, the proximal end of the locking element engaging the plunger rod assembly or the inner surface of the syringe barrel at a surface more proximal than the reduced cross-sectional area of the plunger rod assembly. The elongate body portion of the plunger rod assembly in this embodiment further comprises a plurality of longitudinal vanes arranged to define the recess. The reduced cross-sectional area comprises a notch formed on the plurality of longitudinal vanes, the notch being defined by the boundaries of a pair of substantially parallel wall portions extending inward perpendicularly from an external edge of the longitudinal vanes. The parallel wall portions adjoin a pair of slanted wall portions extending radially inward toward each other from the respective parallel wall portions. The pair of slanted wall portions in this embodiment are preferably joined at a radially inward end of the notch by a wall parallel to the longitudinal vane. Alternatively, the pair of slanted wall portions meet together at a radially inward end of the notch.

In yet another exemplary embodiment, a syringe assembly comprises a syringe barrel having an inside surface defining a chamber, an open end, and a distal end. This embodiment further comprises a plunger rod assembly including an elongate body portion, a recess along the elongate body portion and a stopper connected to the elongate body portion. A plurality of first teeth are formed on the elongate body portion bounding the recess, the first teeth defining a plurality of distally facing shoulders. The plurality of distally facing shoulders are preferably substantially equally spaced along the elongate body portion, wherein the elongate body portion further comprises a second tooth defining an intermediate distally facing shoulder provided between a first and second distally facing shoulder. This exemplary embodiment also includes a locking element slidably positioned within the chamber. The locking element engages the inner surface of the syringe barrel such that the locking element is substantially immovable in the direction of the open end of the syringe barrel. The locking element further engages the plunger rod assembly such that the plunger rod assembly and locking element are movable distally together toward the distal end of the syringe barrel. The exemplary locking element includes a body portion having a proximal end, the proximal end of the locking element engaging the plunger rod assembly or the inner surface of the syringe barrel at a surface more proximal than the reduced cross-sectional area of the plunger rod assembly. In this embodiment, the first and second distally facing shoulders are preferably positioned most distally on the elongate body portion among the plurality of distally facing shoulders. The elongate body portion of the exemplary plunger rod assembly further includes a portion of reduced cross-sectional area configured to break upon the application of excessive axial or torsional force to the plunger rod assembly. The reduced cross-sectional area of the plunger rod is preferably provided near a distal end of the elongate body portion of the plunger rod assembly. The distal end comprises a portion extending proximally from the stopper to the first distally facing shoulder defined by a distal most first tooth of the plurality of first teeth formed on the elongate body portion. In another embodiment, the portion of reduced cross-sectional area is provided on a plurality of positions along the elongate body portion of the plunger rod assembly. In yet another embodiment the portion of reduced cross-sectional area is defined by a hole provided in a longitudinal wall defining the elongate body portion.

Other objects, advantages and salient features of the invention will become apparent to those skilled in the art from the following detailed description, which, taken in conjunction with annexed drawings, discloses exemplary embodiments of the invention.

BRIEF DESCRIPTION OF THE DRAWINGS

The above and other exemplary features and advantages of certain exemplary embodiments of the present invention will become more apparent from the following description of certain exemplary embodiments thereof when taken in conjunction with the accompanying drawings in which:

FIGS. 5a-5d are a set of views of the exemplary single-use syringe of FIG. 3 depicting the placement of a locking element on the plunger rod for providing a plurality of different dosage volumes;

Throughout the drawings, like reference numerals will be understood to refer to like elements, features and structures.

DETAILED DESCRIPTION OF EXEMPLARY EMBODIMENTS

The matters exemplified in this description are provided to assist in a comprehensive understanding of exemplary embodiments of the invention with reference to the accompanying drawing figures. Accordingly, those of ordinary skill in the art will recognize that various changes and modifications of the exemplary embodiments described herein can be made without departing from the scope and spirit of the claimed invention. Also, descriptions of well-known functions and constructions are omitted for clarity and conciseness.

The improvements and advantages of the exemplary embodiments of the present invention are described in view of known prior art devices. The exemplary embodiments of the present invention are improvements adapted from an existing single-use syringe sold by the present assignee, Becton, Dickinson and Company, under the name SoloShot™ IX Auto-Disable Syringe, and from the assignee's U.S. Pat. No. 6,790,197, which is incorporated by reference herein. The following background discussion of a prior art device is based on the description provided in the above patent.

Figure 1A:
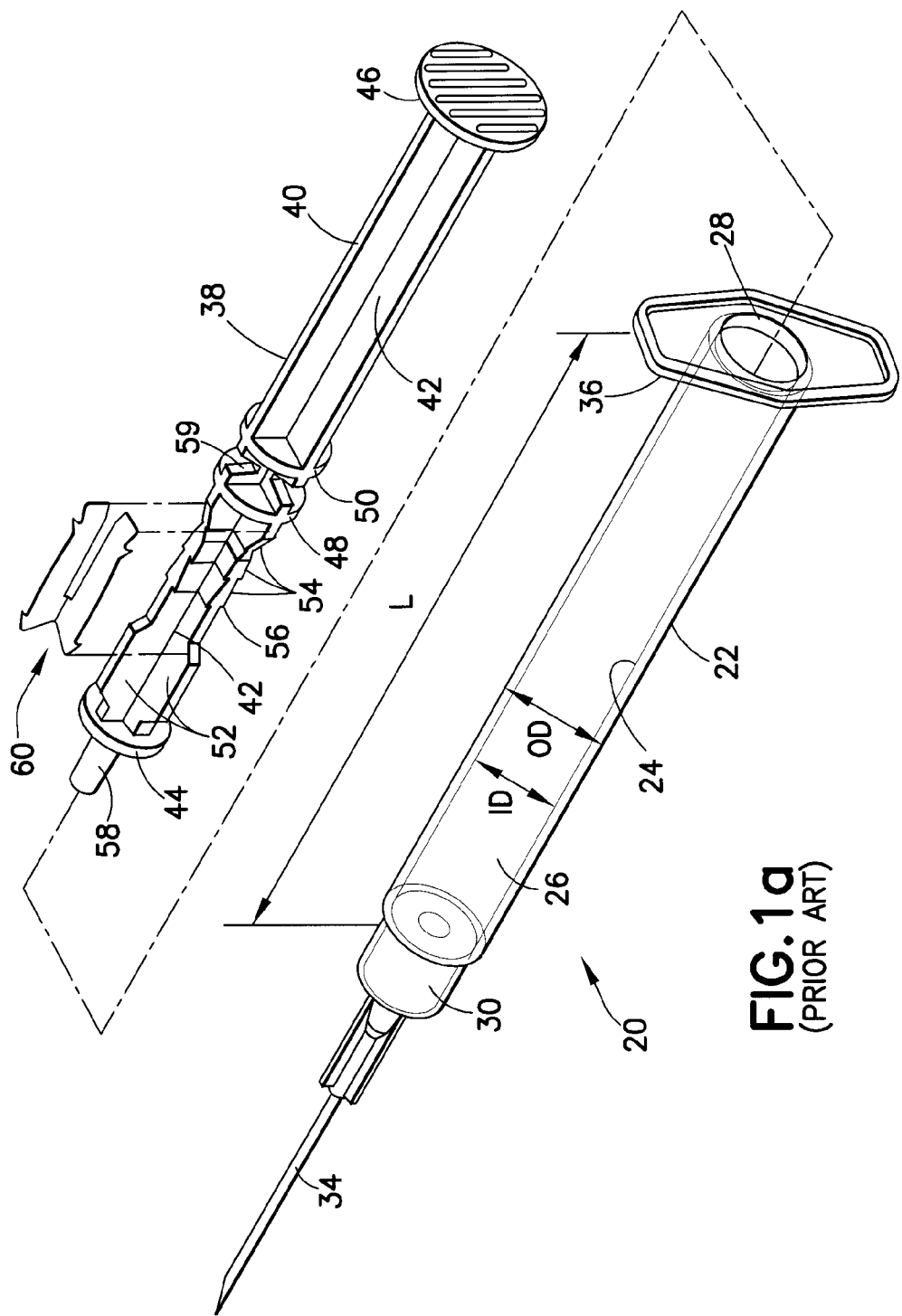
FIGS. 1a and 1b are exploded, perspective views showing two versions of an existing single-use syringe assembly with a barrel, and optionally a plunger rod, having a known size and length-to-diameter ratio.
Figure 2:
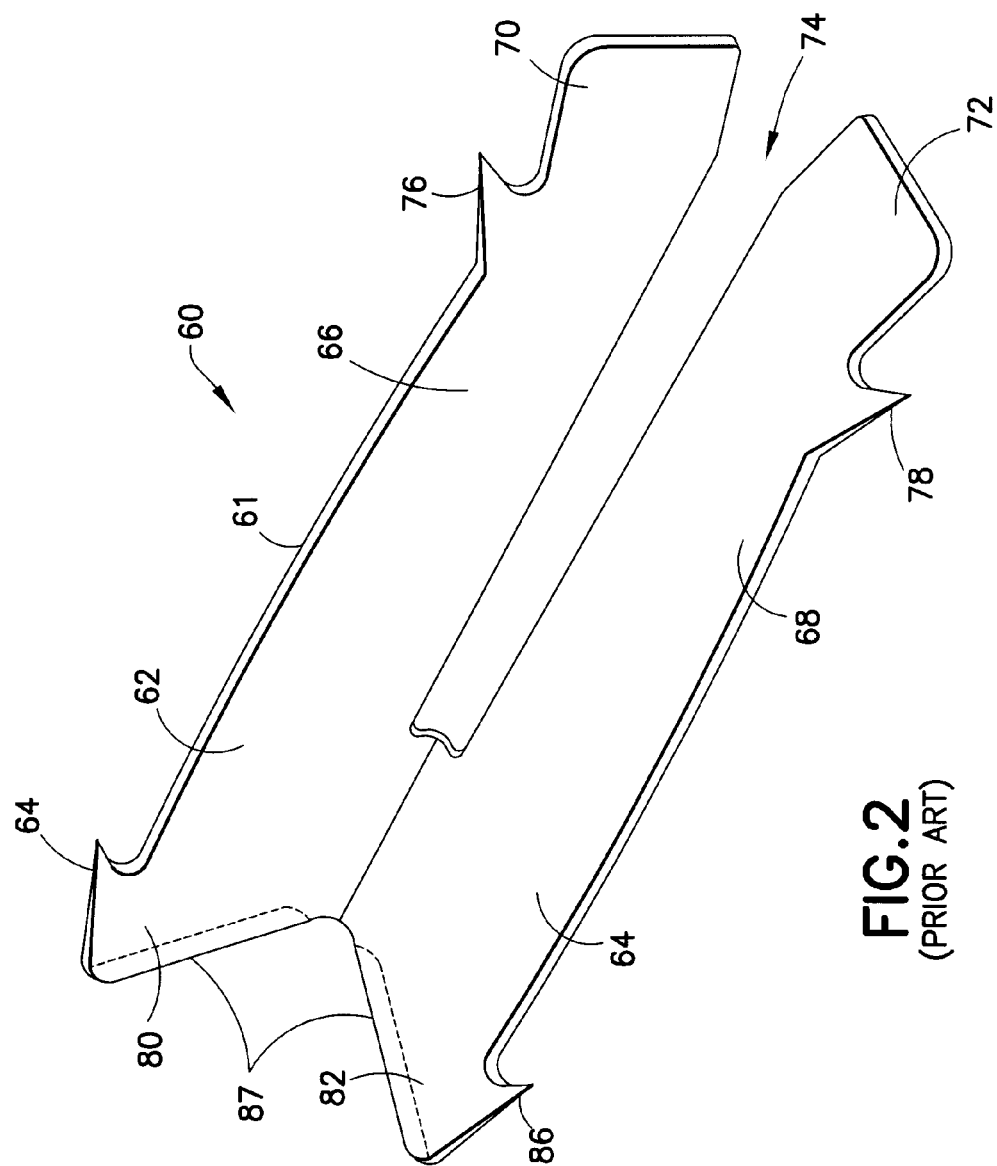
FIG. 2 is an enlarged view of a locking element usable in the single-use syringe assembly of FIG. 1.

Referring first to FIGS. 1a and 2, a single-use syringe assembly 20 includes a barrel 22 having an inside surface 24 defining a chamber 26 for retaining fluid. The barrel 22 includes an open end 28 and a distal end 30 having a passageway therethrough in communication with the chamber. The proximal end of the barrel 22 includes a flange 36 to facilitate handling and positioning of the syringe assembly and to maintain the relative position of the barrel with respect to the plunger rod during medication filling and administration. A needle cannula 34 projects outwardly from the distal barrel end. The needle cannula has a lumen (not shown) therethrough in fluid communication with the passageway and a sharpened distal tip. The syringe assembly of the prior art embodiment is shown with a needle cannula assembly that is permanently attached to the distal end of the barrel. Such a high-quality, permanently attached needle is designed to provide greater patient comfort and may also be provided in exemplary embodiments of the present invention. However, it is also within purview of exemplary embodiments of the present invention to include syringe barrels having removably affixed needles or needle hub assemblies, or fixed or removable blunt cannulas.

As used in the preceding paragraph and hereafter, the term "distal end" refers to the end furthest from the person holding the syringe assembly. The term "proximal end" refers to the end closest to the holder of the syringe assembly.

A plunger rod assembly 38 used in the syringe assembly 20 includes an elongate body portion 40 including at least one and preferably a plurality of elongate recesses 42. The distal end of the elongate body portion includes an integral plunger head or stopper 44. A disc-shaped flange 46 is provided at the proximal end of the plunger rod for allowing the user to apply the force necessary to move the plunger rod with respect to the barrel. The elongate body portion 40 includes a pair of discs 48, 50 intermediate the proximal and distal ends thereof. Cut-outs 59 are provided on the elongate body portion 40, intermediate discs 48 and 50, to produce a reduced cross-sectional area in the plunger rod. This reduced cross sectional area is weak enough to break upon application of excessive bending or rotational force applied to the plunger rod in an attempt to re-use the syringe assembly. The section between the relatively proximal disc 50 and the flange 46 includes radially extending walls or vanes 52 that define portions of the elongate recesses 42. The section adjoining the relatively distal disc 48 has radially extending walls or vanes 52 that define one or more ratchet-like teeth 54. Each tooth 54 includes a distally facing surface or shoulder 56. A frusto-conical nose portion 58 forms the distal end of the plunger rod assembly. It will be appreciated that while the plunger rod assembly of the prior art is shown and described herein as being of integral construction, the plunger rod assembly of the prior art and exemplary embodiments of the present invention may in fact be comprised of two or more separate elements. The plunger head or stopper may, for example, be a separate component made from a material that is different from the material comprising the remainder of the plunger rod assembly, such as a flexible stopper, O-ring or the like.

A locking element 60 is positioned within barrel 22 and within elongate recess 42 in the plunger rod assembly 38. The recess 42 acts as a pathway for longitudinal motion of the locking element relative to the plunger rod assembly. The locking element 60, as best shown in FIG. 2, includes a generally V-shaped body portion 61 comprising first and second radially extending walls 62, 64 joined along a longitudinal axis. A first leg 66 extends proximally from the first wall and a second leg 68 extends proximally from the second wall 64. The legs flare outwardly with respect to the V-shaped body portion 61. The legs 66, 68 are preferably longer than the length of the body portion 61.

Each of the legs 66, 68 include a proximal end portion 70, 72 that is angled toward one of the radially extending walls 52 of the plunger rod assembly. They further include inner and outer edges. (The terms "inner" and "outer" are relative terms as used herein.) The inner edges thereof are substantially adjacent to each other, separated by a longitudinal gap 74. Barbs 76, 78 are integral with the outer edges of the first and second legs. The barbs face proximally, and are preferably located slightly distally of the angled end portions 70, 72. The barbs in exemplary embodiments of the present invention may be different in appearance from those shown in the prior art drawings so long as they are capable of engaging the inside surface 24 of the syringe barrel to prevent proximal movement of the locking element. The barbs are preferably made from a harder material than the barrel, which enhances their ability to resist proximal movement.

In the illustrated prior art embodiment, a second pair of legs extends distally from the V-shaped body portion 61. One of these legs 80 extends from the first wall 62 and the other leg 82 extends from the second wall 64. Legs 80 and 82 preferably include barbs 84 and 86 respectively. Barbs 84, 86 extend proximally from the distal ends of the legs 80, 82. As shown, the barbs are formed on the outer edges of the distally extending legs 80, 82.

The locking element 60 is preferably formed from a thin sheet of metal such as stainless steel. The dimensions of the locking element are selected in accordance with the barrel and plunger rod assembly with which it is to be used. The angle formed between the two halves of the locking element in the shown embodiment is about 90 degrees, and may desirably be about 100 degrees. When placed in one of the recesses 42 in the plunger rod assembly, the locking element will accordingly exert a force against the two adjoining walls 52 that define the recess. Accordingly, gap 74 is maintained between the legs 66, 68 even after installation of the locking element. The maintenance of the gap acts as a cantilever spring, such that it provides a relatively reduced force on the barrel and facilitates use and installation of the locking element 60 in the syringe barrel.

Locking element 60 comprises at least one cutting edge for disabling the plunger head or stopper 44 that is preferably formed by providing a bevel on one side of the thin sheet of metal making up the locking element. As used herein the term cutting edge or cutter is intended to include cutting edges and/or pointed projections or any other structure capable of cutting through or piercing the plunger head or stopper. It will be appreciated that the locking element could be worked by grinding or other means on both sides thereof to form cutting edges. The prior art embodiment, as shown, contains two cutting edges 87, one on each of the legs 80 and 82. Alternatively, a distally extending barb on leg 80 and/or leg 82 or other cutting member can be provided on the locking element for piercing or cutting the plunger head or stopper 44. In the prior art embodiment, distal barbs 84 and 86 stabilize the cutting edge to help it cut the plunger head or stopper 44.

The syringe assembly is easily constructed from the component parts thereof. Locking element 60 is positioned in one of the recesses 42 in the plunger rod assembly such that the angled end portions of legs 66, 68 adjoin the relatively distal disk 48, as shown in FIG. 1a. Legs 66 and 68 extend proximally, and barbs 76, 78, 84, 86 are angled proximally with respect to the plunger rod assembly. The plunger rod/locking element assembly is then inserted into barrel 22 through the proximal end thereof. As the assembly is moved distally within the barrel, the angular orientation of the barbs allows them to slide along while engaging inside surface 24 of the barrel. The locking element moves distally with the plunger rod due to the engagement of the ends of the legs 66, 68 with disc 48. The plunger rod/locking element assembly is moved distally, until the plunger head or stopper engages the end wall of the barrel. It is then ready for use or storage. A needle cover (not shown) can be mounted to the distal end of the barrel to protect the needle cannula. The cover is then removed prior to use.

In use, plunger rod assembly 38 is retracted from a starting position to a second position in order to draw fluid through needle cannula 34 and into chamber 26 of barrel 22. Locking element 60 remains stationary during such retraction, and the plunger rod assembly is moved proximally with respect to both barrel 22 and the locking element. This is due to the engagement of the barbs 76, 78, 84, 86 with the inside surface 24 of the barrel. While the prior art embodiment illustrates four barbs, the locking element can function with more barbs or as few as one barb. The number and placement of the barbs is chosen to enhance performance. The angled ends 70, 72 of the legs 66, 68 of the locking element ride over the teeth 54 of the plunger rod assembly during retraction thereof. The multiple teeth are intended to prevent recycling the plunger rod in mid-stroke. During retraction of the plunger rod, the user may feel and/or hear the movement of the legs as they ride over the teeth 54.

Retraction of the plunger rod assembly 38 is limited by the locking element 60. The proximal surface of the plunger head or stopper 44 engages the distal end of locking element 60. The user can feel this engagement. However, cutting edges 87 do not penetrate the plunger head or stopper 44 as a result of the forces exerted during normal use. As the locking element 60 cannot be moved proximally, further retraction of the plunger rod assembly is not possible without applying extra axial force that would damage the plunger head or stopper 44 by allowing the cutting edges 87 to cut the plunger head or stopper 44. The amount of fluid that can be drawn into the chamber 26 is accordingly limited by the distance between the proximal surface of the plunger head or stopper 44 and the disc 48 as well as the length of the locking element 60. It will be appreciated that the distance between the plunger head or stopper 44 and the relatively distal disc 48 and the length of the locking element 60 can be chosen to meet the needs of particular applications such as fill volumes of 0.01 ml, 0.05 ml, 0.5 ml, 1.0 ml and 2.0 ml. Additionally, the syringe can be provided to the end user as a prefilled syringe, in which case retraction of the plunger rod assembly would not be necessary or possible.

Once the fluid has been drawn into the barrel from a vial or other fluid source, the needle cannula can be removed from the fluid source and used for injection. During the injection of a patient, the plunger assembly 38 and locking element 60 both move distally upon an axial force applied by the user or clinician. At the end of the injection stroke, plunger head or stopper 44 again adjoins or engages the end wall of barrel 22. The locking element remains preferably positioned with the distal end contacting the plunger head or stopper 44 and the proximal end engaging the most distal tooth or ratchet 54 of the plunger rod. The distance between the most distal tooth 54 and the plunger head or stopper 44 is ideally the length of the locking element 60, so as to force the distal end of the locking element to engage the plunger head or stopper after the locking element rides over the most distal tooth, thus preventing any further withdrawal of the plunger rod at the end of the injection stroke. After a proper dose administration, both the plunger rod assembly 38 and the locking element 60 are substantially immovable from their positions. The syringe assembly 20 accordingly cannot be re-used. Should a person use extraordinary axial force in an attempt to retract the plunger rod assembly from the end position, cutting edges 87 at the distal end of the locking element will penetrate the plunger head or stopper 44, rendering it unusable. Disabling of the plunger head or stopper preferably occurs when the force exerted is sufficient to dislodge the locking element in the proximal direction, or a slightly lesser force. As discussed above, simple engagement of the cutting edges and plunger head or stopper should not compromise the integrity of the plunger head or stopper. Further, should a person apply an excessive rotational or bending force to the plunger rod in an attempt to dislodge the locking element 60 or otherwise attempt to re-use the syringe assembly, the reduced cross-sectional area provided by cut-outs 59 of the plunger rod will cause the plunger rod to break thus rendering the syringe assembly unusable.

Figure 1B:
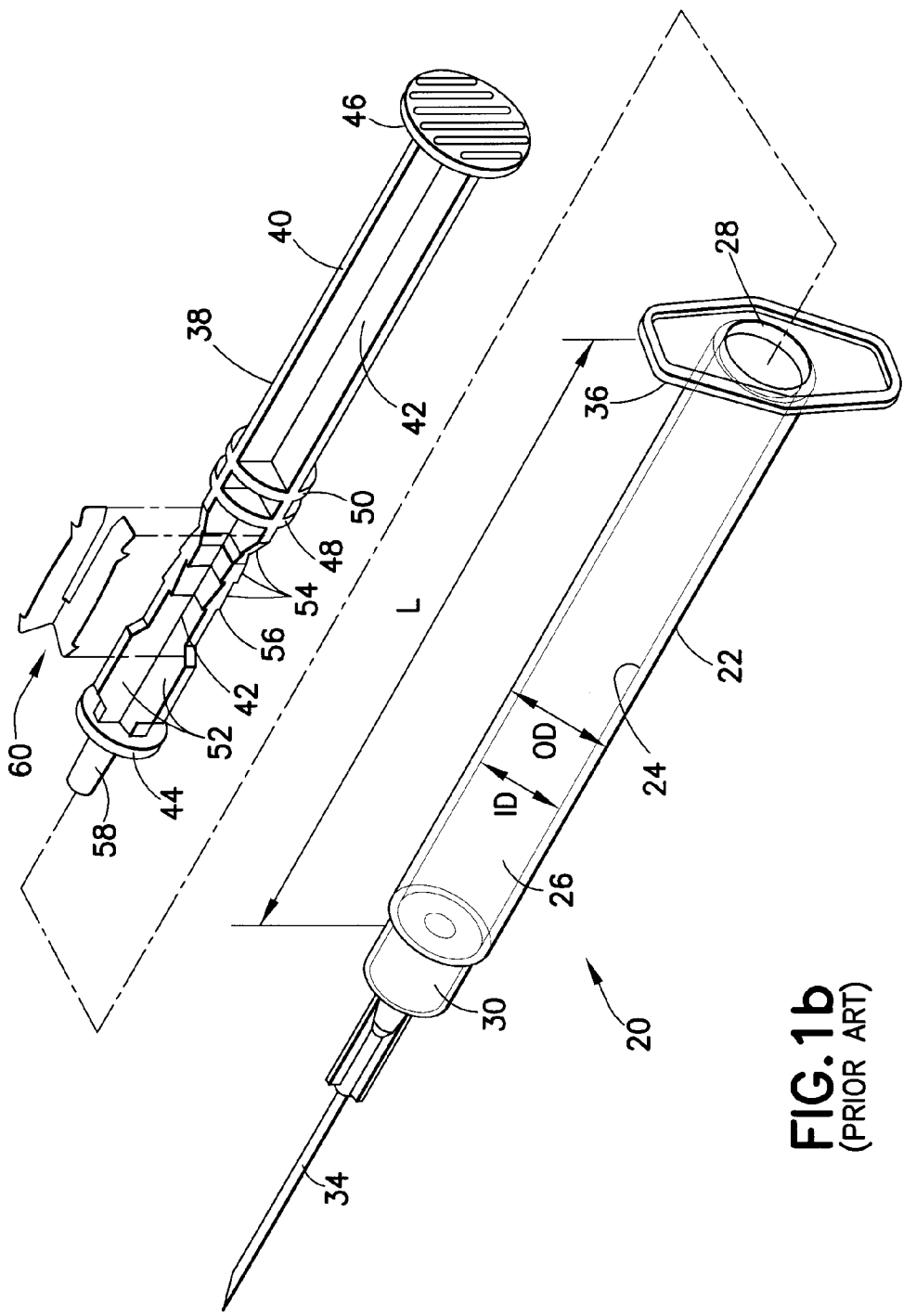

FIG. 1b illustrates a syringe assembly similar to the embodiment depicted in FIG. 1a. This alternate syringe embodiment corresponds to the product commercially sold by the present assignee, Becton, Dickinson and Company, under the name SoloShot™ IX Auto-Disable Syringe. The embodiment depicted in FIG. 1b differs from the embodiment discussed above, primarily in that the cut-outs 59 are removed from the plunger rod. Additionally, the commercial embodiment does not utilize the optional cutting edge 87 provided on the distal end of the locking element, for cutting the plunger head or stopper 44.

The above described syringe assemblies are effective for their intended uses. Nevertheless, as previously discussed, an improved, smaller, more cost effective device is still needed. Exemplary embodiments of the present invention with improvements over the above-discussed single-use syringes will now be discussed. Like reference numerals of the above-discussed prior art devices will be used to describe similar components of exemplary embodiments of the present invention. Alternative embodiments and functionality discussed above with respect to the prior art devices are also applicable to exemplary embodiments of the present invention where relevant.

While the exemplary embodiments and features described herein are advantageously directed to a syringe assembly of reduced size, one skilled in the art will appreciate that such embodiments and features are not limited to a syringe assembly of reduced size relative to the prior art and may be utilized in a syringe assembly of any desired size.

The improved features and functionality of exemplary embodiments of the present invention are a result of the reduction in size of the preferred syringe assembly relative to the prior art devices. An exemplary embodiment of the present invention functions very similarly as those described above, yet can be greatly reduced in size. At least the barrel and preferably the plunger rod, can be configured to have an optimized size and length-to-diameter ratio to allow reductions in construction material and other costs related with a larger device. For example, the prior art devices of FIGS. 1a and 1b comprise a length L of approximately 51.40 mm, and an inside diameter ID of approximately 8.73 mm and outside diameter OD of approximately 9.84 mm. To improve such an exemplary configuration to achieve the desired goals of reduced size and waste, and reduce injection anxiety, while maintaining effective functionality, an optimized size and length-to-diameter ratio is obtained. For example, the exemplary device of FIG. 3 can comprise a length L' of approximately 47.82 mm, and an inside diameter ID' of approximately 4.70 mm and outside diameter OD' of approximately 5.90 mm. The use of an exemplary barrel having such a size and length-to-diameter ratio can result in a device that is up to 3.5 times smaller than similar injection devices. The reduction in diameter of the barrel enables a reduction in the wall thickness of the barrel with equivalent rigidity, since generally, smaller diameter barrels are stiffer than larger diameter barrels. For example, the exemplary devices of FIGS. 1a and 1b can comprise a barrel wall thickness of approximately 0.69 mm, while the exemplary device of FIG. 3 can comprise a barrel wall thickness of approximately 0.61 mm. Such values provide an optimized sized device with sufficient size and strength to satisfy a user, and to minimize the use and therefore cost of construction materials.

While the optimized length-to-diameter ratio of the barrel in an exemplary embodiment of the present invention is shown to be cost effective, the reduction in barrel size can undesirably reduce the volume of fluid that is capable of being drawn into the chamber 26 during the aspiration stroke. Use of plunger rod 38, as shown in FIGS. 1a and 1b and described above, in an exemplary embodiment of the present invention would unsatisfactorily limit the range of doses capable of being provided by an exemplary syringe assembly. Accordingly, it is desirable to increase the distance of retraction of the plunger head or stopper 44 in the aspiration stroke in order to draw in a desired volume of fluid. The distance of retraction, and therefore the volume of fluid, in the prior art devices is limited by the placement of the distal disc 48 and the length of the locking element 60. As such, the prior art plunger assembly utilized in the exemplary barrel 22' of reduced diameter would be incapable of delivering greater dose sizes such as 0.5 ml and 1.0 ml.

Figure 4:
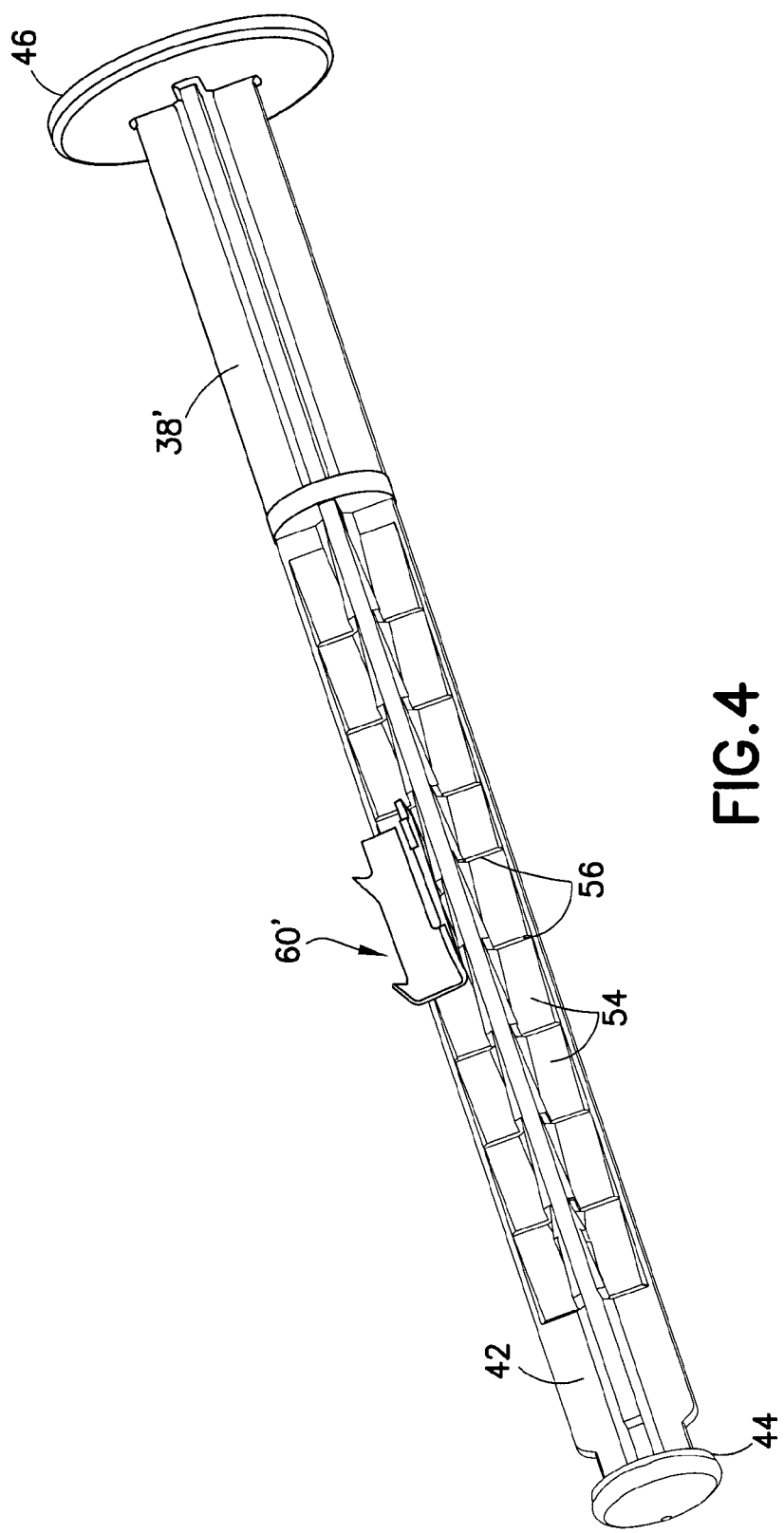
FIG. 4 is an enlarged view of a plunger rod usable in the single-use syringe of FIG. 3 including a locking element positioned on the plunger rod for controlling the dosage volume of the single-use syringe.
Figure 5C:
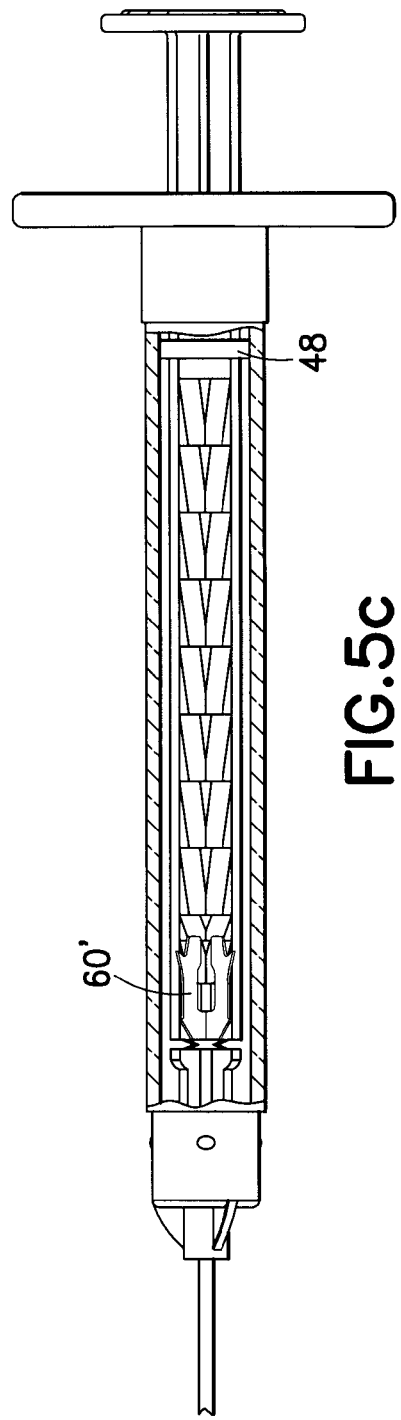

In a smaller-diameter syringe of the exemplary embodiment, it is desirable to provide a plunger rod 38', as best shown in FIG. 4, for enabling an increased distance of retraction and therefore a wider range of dose sizes. Further, the use of an exemplary barrel having such a size and length-to-diameter ratio results in better volume control in that an intended dose size can be more accurately controlled within acceptable error and in that dead space is minimized, thereby minimizing vaccine waste. The plunger rod 38' in FIG. 4 includes a plurality of teeth 54 preferably positioned along the elongate recess 42 of the plunger rod for a length substantially equivalent to the length of the barrel 22'. Such a plunger rod construction enables a variety of fluid volumes to be drawn into the chamber 26 as determined by the initial position of the locking element 60' as shown in FIGS. 5*a*-5*c*.

Figure 5D:
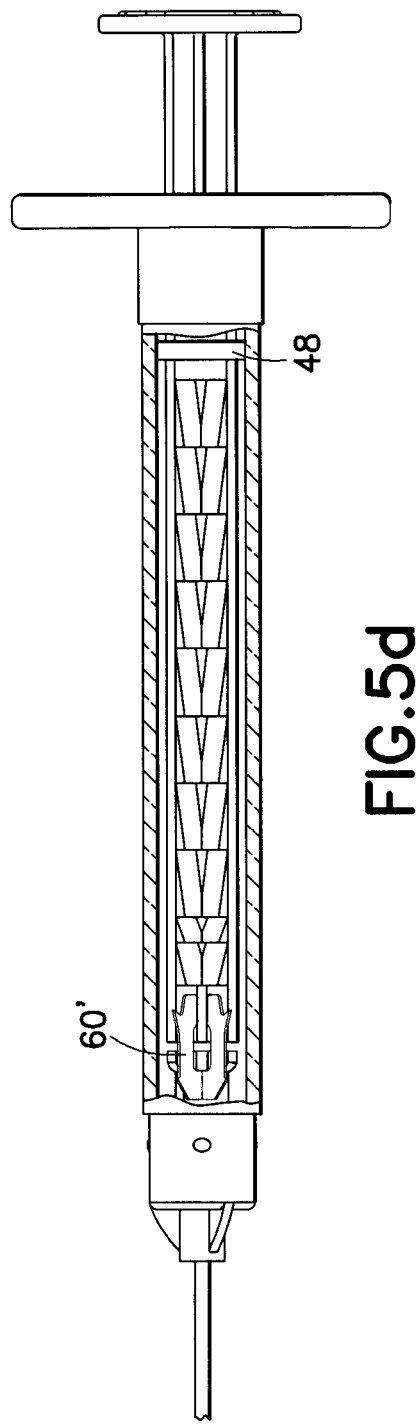

Each of the intended maximum volumes that can be obtained are designed into the syringe and are determined by the initial placement of the locking element 60' relative to the plunger rod during manufacture and assembly. For example, as seen in FIG. 5*a*, to obtain a 0.5 ml dose volume, the locking element 60' is placed more proximal (i.e., closer to the flange 36) on the plunger rod. For smaller volumes, as shown in FIGS. 5*b* and 5*c*, the locking element 60' will be placed more distally along the plunger rod and inserted into the barrel, thus limiting the distance of retraction of the plunger head or stopper 44 during the aspiration stroke. As previously discussed, during proper dose setting, the plunger rod 38' is retracted in the proximal direction until the plunger head or stopper 44 engages the distal end of the locking element 60'. It is upon this engagement that the intended dose is set. Regardless of the initial placement of locking element 60' on the plunger rod 38', after administration of a properly set dose, the locking element will have been driven distally along with the plunger rod 38', due to engagement with the distal most step 54, until the plunger head or stopper engages an end wall of the barrel, as shown in FIG. 5*d*. When the locking element 60' is in this final position, the syringe assembly of the exemplary embodiment is rendered unusable. Plunger rod 38' also preferably includes a disc 48 provided on the plunger rod at a position near the open end of the syringe barrel when the plunger rod is fully inserted within the barrel, as seen in FIGS. 5*a*-5*d*. Disc 48 aids in preventing a user from intentionally dislodging the locking element 60' from the syringe barrel by using a tool or device capable of being inserted into the syringe barrel.

In an exemplary embodiment of the present invention, the positioning of locking element 60' on the plunger rod enables a slightly larger dose than a dosage marked on the syringe barrel, preferably about 0.01 ml larger, to fill the barrel chamber 26. In this embodiment, the additional volume enables a user or clinician to deliver an "air shot" to remove any air bubbles that may have entered the syringe chamber 26, without reducing the intended effective dose size.

Figure 6:
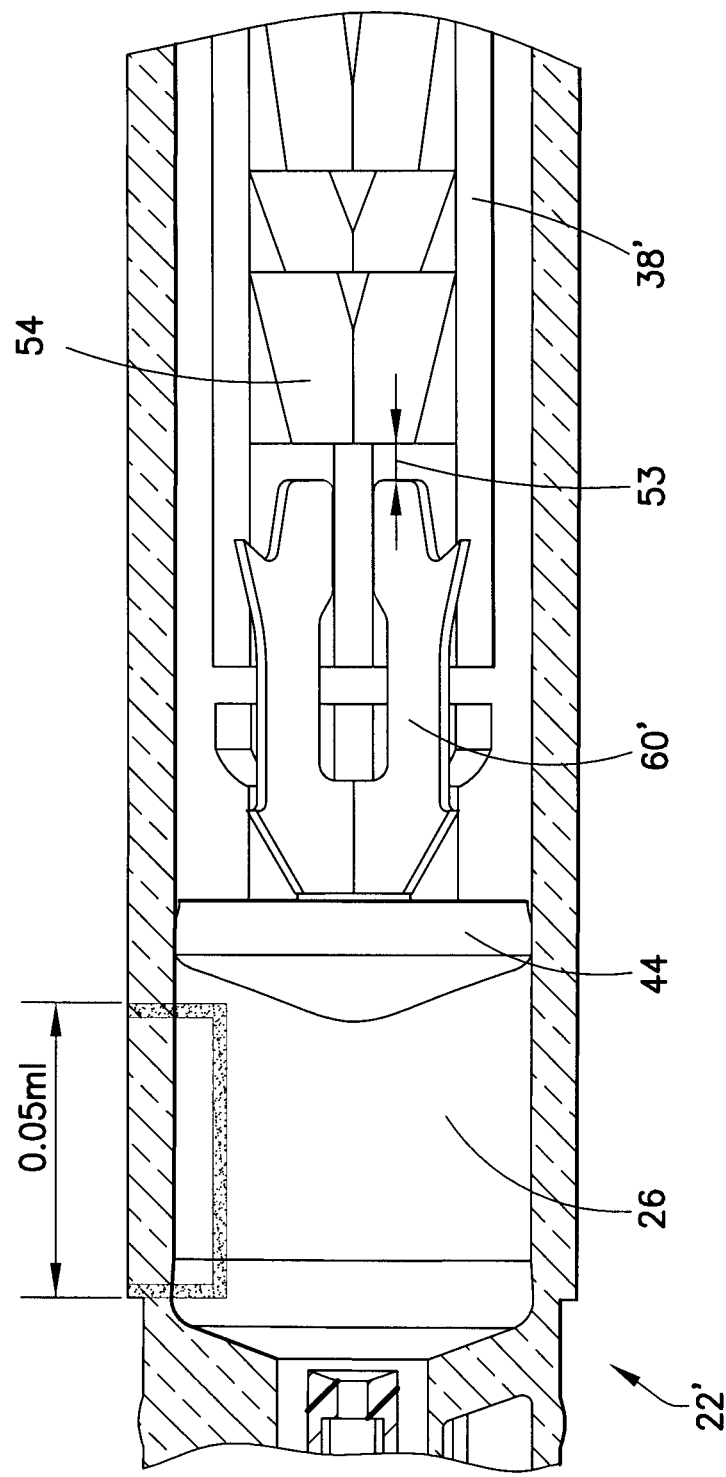
FIG. 6 depicts an exemplary embodiment of the single-use syringe for enabling additional clinical procedures of the single-use syringe.

An additional feature of the exemplary embodiment also enables the user or clinician to perform a "vein check", if necessary, to ensure that the injection of the set dose is effectively administered. This procedure usually requires the user or clinician to slightly withdraw the plunger rod after insertion of the cannula 34 into the skin of the user for detecting an inflow of blood in the distal end 30 of the syringe barrel. If blood is present, the user or clinician can be confident that a vein was penetrated for the injection. This feature is enabled by providing a space along the plunger rod 38' between the plunger head or stopper 44 and the distal-most tooth 54 that is slightly larger than the length of the locking element 60', resulting in the gap 53 as shown in FIG. 6. Because of the gap 53, the user or clinician can deliver the "air shot" without advancing the locking element in the distal direction. The gap 53 then enables the user to withdraw the plunger rod a slight distance, approximately the length of the "air shot", for executing the "vein check." In the prior art devices, the length of this space provided along the plunger rod 38 is substantially the same size as the locking element 60 so as to prevent even a minimal withdrawal of the plunger rod in the proximal direction after an intended dose is set or administered. However, this feature is not necessary due to the reduced barrel diameter of the exemplary embodiment. The gap 53 provided in the exemplary embodiment preferably accommodates no more than about 15 µl of fluid, a negligible volume that does not enable or increase the possibility of potential misuse of the syringe assembly.

The reduction in size of the barrel and plunger rod 38 also requires a reduction in size of the locking element 60. However, simply reducing the scale of the locking element 60 of the prior art device results in greater stiffness of the locking element, and therefore introduces additional resistance that causes excessive injection and aspiration forces that are not only undesirable but may exceed ISO specifications for such a device. It is desirable to provide an effective single-use syringe design while maintaining the usability and "feel" of the syringe. Both flexibility of the locking element (to minimize the forces as the locking element slides distally and as the locking element rides over the teeth 54 during dose setting) and rigidity (to prevent the user from defeating the locking element through the application of axial force or torque) are required. It is desirable to realize an optimal balance between the flexibility and rigidity of an exemplary locking element 60', for use with the exemplary barrel 22' and plunger rod 38', in order for the exemplary syringe device to provide smooth plunger rod movement so that injections can be easily administered by clinicians without a change in technique.

Figure 7A:
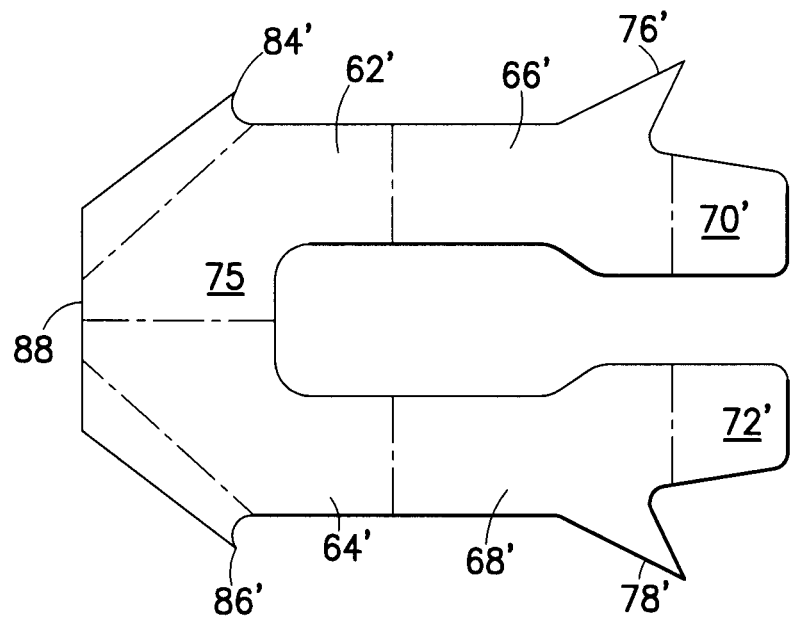
FIGS. 7a-7f depict different views of an optimized locking element usable in the single-use syringe of FIG. 3.
Figure 7B:
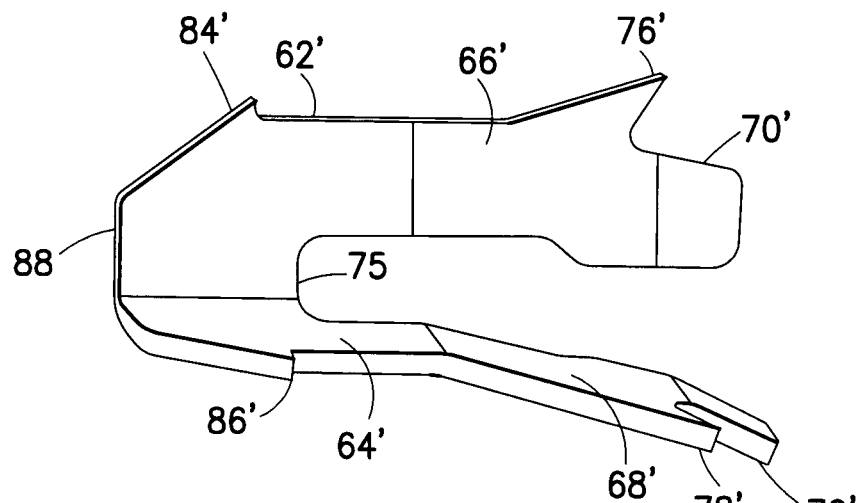
Figure 7C:
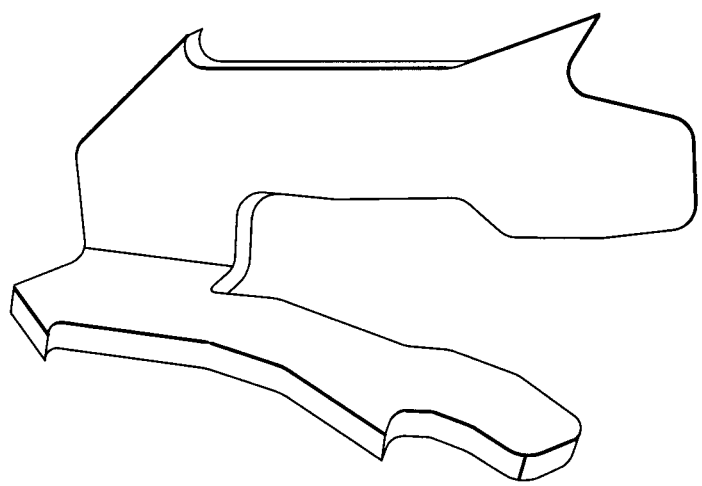
Figure 7D:
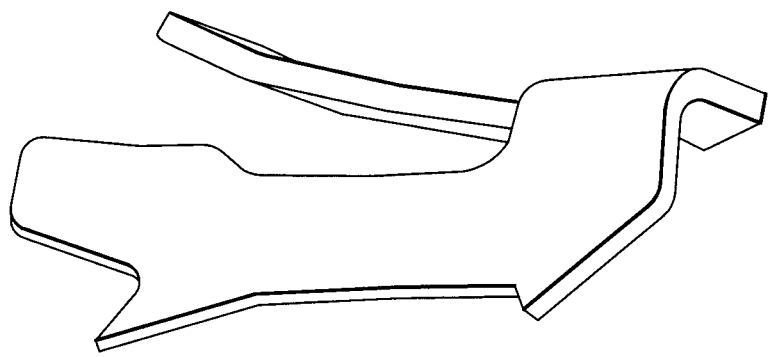
Figure 7E:
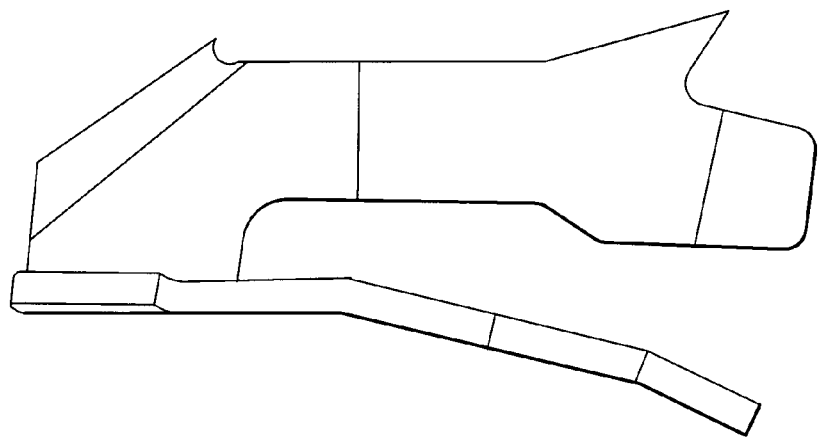
Figure 7F:
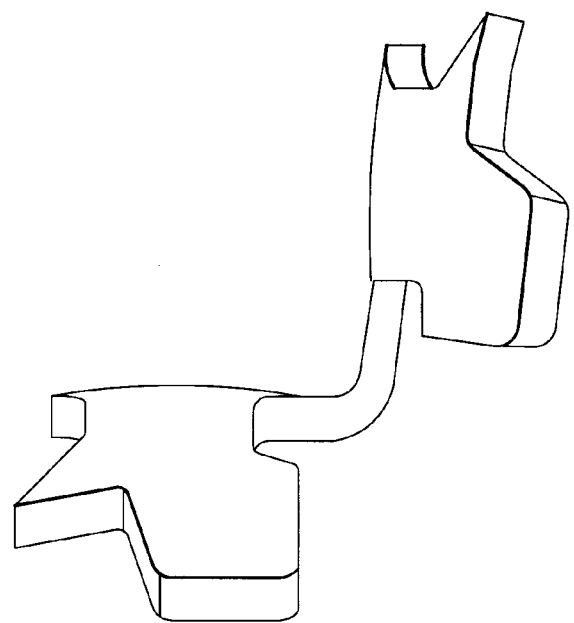

First, several modifications have been made to the prior art locking element 60 for use in the exemplary embodiments of the present invention while maintaining the general shape and functionality of the locking element 60, as shown in FIGS. 7*a*-7*f*. FIGS. 7*a* and 7*b* depict different views of an optimized locking element usable in an exemplary embodiment of the single-use syringe of FIG. 3. In comparison to the locking element 60 of the prior art device, shown in FIG. 2, the locking element of FIGS. 7*a* and 7*b* has a straight, distal edge 88 with a reduced front edge area (relative to the overall width of locking element 60'). This reduced front edge area 88 is optionally sharpened to enhance the ability to cut the plunger head or stopper 44, by concentrating pressure on the plunger head or stopper. The sharpened edge or cutter 88 of an exemplary locking element 60' is an optional feature that may not be necessary, especially in view of improved features of the plunger rod to be discussed below with respect to FIGS. 9-14. The height and angle of distal barbs 84' and 86' are minimized to reduce sliding forces for easier distal movement of the locking device 60' during both assembly and injection. Additionally, the outer edges of proximal end portions 70' and 72' are angled at their respective ends to avoid touching the inner surface of the barrel to further reduce frictional forces when the clip is installed. The angle of the rear barbs 76' and 78' is designed so that the rear barbs effectively dig into the inner surface of the barrel 22' when the plunger rod 38' is retracted, so as to prevent proximal movement of the locking element 60'. The height of the rear barbs 76' and 78' is preferably increased to be larger than the thickness of the barrel wall so that if the locking element 60' is retracted with significant force, the rear spikes will pierce the inner diameter of the barrel 22'. FIGS. 7c-7f provide additional views of the exemplary locking element 60' discussed above.

The above features of locking element 60' are provided for use in an exemplary embodiment of a syringe assembly device. The actual locking element used in the syringe assembly device, however, may include only some or none of the above features, as determined by the requirements of the specific embodiment. For instance, it is within purview of the present application to utilize a locking element comprising distally extending legs 80 and 82, with sharpened points or edges used for penetrating the plunger head or stopper, provided in combination with the angled proximal end portions 70' and 72'. The actual locking element used in the exemplary embodiments is not limited to the relative shapes, sizes and specific features shown in FIGS. 7a-7f.

Figure 8C:
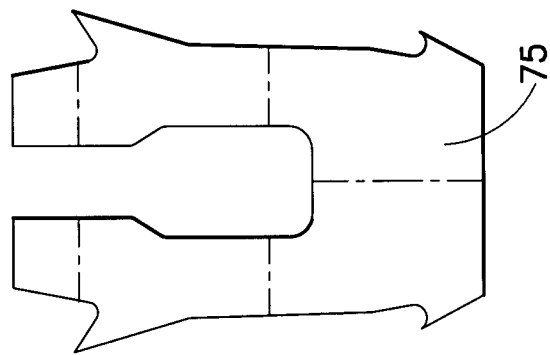
FIGS. 8a-8c depict a plurality of locking elements with varying bridge widths.
Figure 8B:
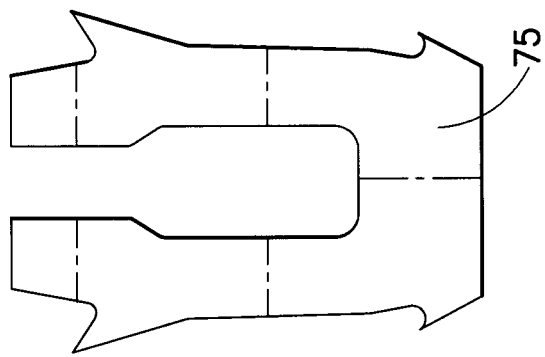
Figure 8A:
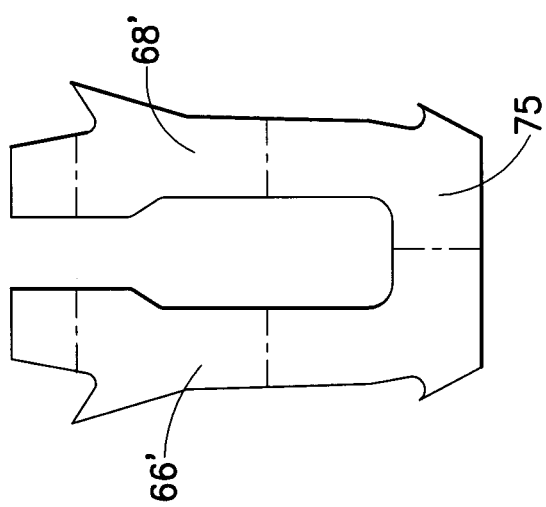

One additional consideration of the improved locking element 60' that is important in determining the flexibility and rigidity characteristic of the locking element 60' discussed above, is the width of a bridge section 75, several versions of which are shown in FIGS. 8a-8c. The width of the bridge section 75 is chosen to provide a desirable balance between flexibility and rigidity. The width of bridge section 75 in FIG. 8a can be reduced so as to increase the length of the proximal legs 166 and 168, thus providing increased flexibility of the locking element 60' which allows for a suitable reduction in injection forces. However, a locking element 60' of such a section width is less rigid and may render the locking element susceptible to a twisting failure under the application of moderate torque to the plunger rod. Users attempting to re-use the exemplary syringe may twist the plunger rod to try to defeat the locking element. Upon such twisting, a less rigid locking element is susceptible to being folded or otherwise disfigured such that it is no longer effective in preventing a subsequent withdrawal of the plunger rod and may even be removed from the syringe barrel altogether. The locking element 60' shown in FIG. 8c has a bridge section 75 of considerably greater width than that of FIG. 8a. While this bridge section dimension considerably reduces the susceptibility of the locking element 60' to twisting failure, such a design may be too stiff and may undesirably increase the injection and aspiration forces. The locking element 60' of FIG. 8b depicts a width of bridge section 75 that is intermediate between the dimensions shown in FIGS. 8a and 8c. Such a dimension yields expected results, such that the flexibility is less than that of FIG. 8a, but greater than that of FIG. 8c. The version of locking element 60' shown in FIG. 8b, also has an improved rigidity from that of FIG. 8a, but is not as rigid as the locking element shown in FIG. 8c. In an exemplary embodiment, the overall length of the locking element 60' is preferably about 5.59 mm. In this embodiment, the width of the bridge section 75 is preferably no larger than approximately 1.524 mm, such that the locking element is not too stiff. Thus, in this embodiment, the length of the bridge portion is about 27% (1.524 mm/5.59 mm=27.263%) of the length of the locking element.

While the locking element 60' shown in FIG. 8b can represent a desirable balance between the versions of FIGS. 8a and 8c, the resultant flexibility and rigidity characteristics may not, in and of themselves, provide the desired injection performance in an exemplary embodiment of the present invention. Therefore, in an exemplary embodiment of the present invention, the plunger rod 38' is preferably modified to further complement the performance characteristics of the locking element 60' to achieve the desired results. Ultimately, the optimal design among those of FIGS. 8a-8c will be chosen by balancing the desire for reduced injection and aspiration forces with the desire to render the locking element 60' less susceptible to twisting failure as determined by the particular combination with one of the exemplary modified plunger rods described below.

Figure 9:
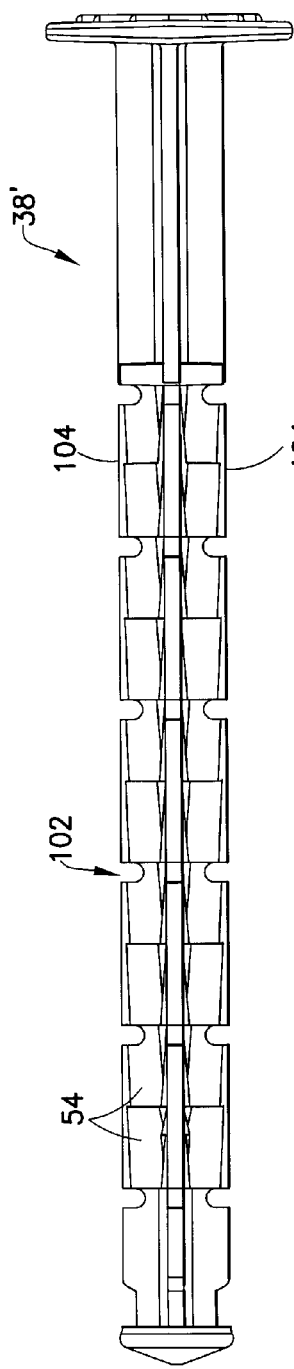
FIG. 9 is a view of an alternative plunger rod for use in the single-use syringe of FIG. 3 with a plurality of notches forming a reduced cross-sectional area of the plunger rod.

An exemplary embodiment of the present invention preferably utilizes the modified plunger rod 38' shown in FIG. 9 for complementing the performance characteristics of the improved locking element 60'. Namely, it is desired to provide an effective locking element 60' with sufficient flexibility yet overcome the problem discussed above with respect to the susceptibility to failure of such a locking element 60'. The plunger rod 38' of FIG. 9 is similar to the plunger rod of FIG. 4 except for the addition of a plurality of U-shaped notches 102 formed on the cruciform plunger rod for reducing the cross-sectional area of the plunger rod. The elongate body portion of plunger rod 38' is preferably of cruciform shape with longitudinal vanes 104 extending along the body. An exemplary embodiment of the present invention includes at least one notch 102 provided on the longitudinal vanes. The notch 102 is preferably formed on the edge of the vane 104 and extends radially inward toward the cruciform intersection as shown in FIG. 9. It is preferable that a similar notch be formed on each of the remaining longitudinal vanes 104 in a matching position along the edge of the vane, producing a reduced cross-sectional area in the plunger rod. The reduced cross-sectional area weakens the plunger rod 38', causing its destruction if an excessive axial or rotational force is applied to the plunger rod in an attempt to re-use the syringe or otherwise defeat the locking element 60', thus preventing re-use of the exemplary syringe assembly. Since a locking element can be placed in a plurality of positions along the plunger rod as shown in FIGS. 5a-5c, it is desirable for the plunger rod 38' to be breakable at a plurality of positions regardless of the placement of the locking element. Accordingly, an exemplary embodiment of the present invention includes a plurality of notches spaced along the longitudinal vane 104 providing a plurality of reduced cross-sectional areas as seen in FIG. 9. Preferably, one set of aligned notches is provided at every second plunger tooth 54 as shown in FIG. 9. Further, because of the potential use of the entire length of the plunger rod 38' in an exemplary embodiment, such a plurality of positions of the notches 102 along the plunger rod should not interfere with the intended operation of the locking element 60'. Such notches 102 of the exemplary embodiment are advantageous over the cutouts 59 of the prior art device in that the reduced cross-sectional areas of the plunger rod 38' do not limit the useable length of the plunger rod for administering a range of desired doses such that they do not interfere with the positioning of the locking member 60' on the plunger rod.

Figure 3:
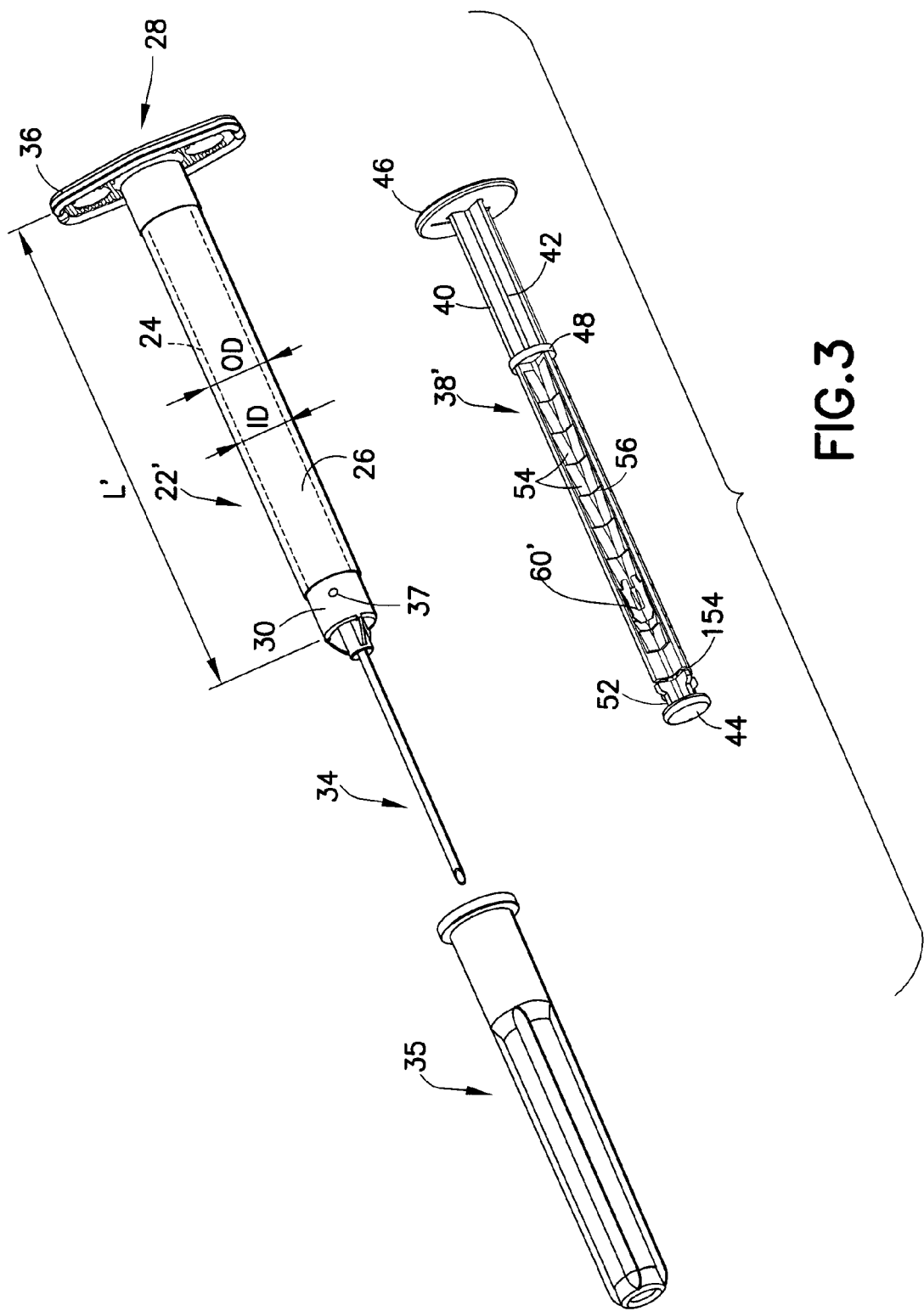
FIG. 3 is an assembly view showing a single-use syringe according to an embodiment of the present invention with a barrel, and optionally a plunger rod, having an optimized size and length-to-diameter ratio.

The plunger rod 38' of FIG. 9 is preferably usable with the syringe assembly shown in FIG. 3. Due to the plurality of reduced cross-sectional areas, an excessive torque applied to the plunger rod will now lead to destruction of the plunger rod at a force less than that required for the locking element to fail. Thus, the above described problem of undesirable twisting failure of the locking element 60' shown in FIGS. 8a-8c can be avoided without resorting to a stiffer version of locking element 60' that produces undesirably high injection and aspiration forces. The reduced cross-sectional areas of the exemplary embodiment supplement the performance of the locking element 60' by reducing a desired rigidity of the locking element 60'. Such an exemplary notched plunger rod enables the syringe assembly to operate with reduced injection and aspiration forces by utilizing a locking element 60' with an optimal flexibility realized by a reduced bridge width 75 as shown in FIG. 8*a* or 8*b*.

Figure 10:
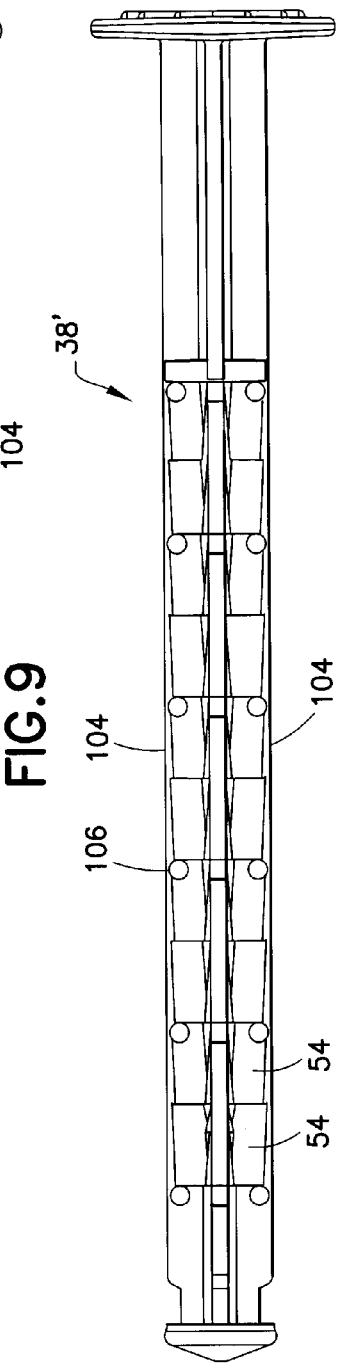
FIG. 10 is a view of an alternative plunger rod for use in the single-use syringe of FIG. 3 with a plurality of holes forming a reduced cross-sectional area of the plunger rod.

FIG. 10 shows an additional exemplary embodiment of the present invention that is also effective in solving the problem of twisting failure of the locking element 60'. A plunger rod 38' as shown, includes holes 106 in the longitudinal vanes 104 as opposed to the previously described notches. Such a plunger rod provides functionality and advantages similar to those of the embodiment shown in FIG. 9, namely, destruction of the plunger rod 38' prior to failure of the locking element 60' under excessive torque. Yet this exemplary embodiment provides additional rigidity and better control of the plunger rod 38' during the aspiration and injection strokes. Such additional rigidity requires a greater force for destruction of the plunger rod 38', which may require a locking element 60' of increased rigidity. However, such an exemplary embodiment is still advantageous over the prior art for similar reasons discussed above.

The exemplary plunger rods discussed above, with respect to FIGS. 9 and 10, are effective in preventing re-use of an exemplary syringe while complementing the performance characteristics of the exemplary locking element 60' such that the forces on the plunger rod required during aspiration and injection are satisfactory. However, because of the plurality of reduced cross-sectional areas provided along the plunger rod 38', the plunger rod may not be of sufficient axial rigidity and may be susceptible to accidental failure during normal use of the syringe device. The above exemplary plunger rods are most susceptible to failure at a reduced cross-sectional area that is more proximal relative to the position of an exemplary locking element 60'. This is due to the fact that the locking element 60' supports the plunger rod 38' with respect to the barrel 22', such that a rotational force on the plunger rod is transferred to the locking element. Thus, the portion of the plunger rod 38' that is more distal relative to the locking element experiences a lesser rotational force than the plunger rod portion that is more proximal than the locking element 60'. As such, the more proximal portion of the plunger rods 38', as shown in FIGS. 9 and 10, may be vulnerable to accidental failure, upon incidental rotational forces applied during normal use.

In another exemplary embodiment of the present invention, as shown in FIGS. 11-14, the plunger rod 38' includes an improved frangible or breakable section to prevent potential re-use of the syringe, while strengthening the plunger rod against accidental failure. The plunger rod 38' in this embodiment also includes a plurality of teeth 54 positioned along the elongate recess of the plunger rod for a length substantially equivalent to the length of the exemplary barrel 22', similar to the embodiment shown in FIG. 4. Also similar to the embodiment shown in FIGS. 4 and 5, an exemplary locking element 60' is disposed at a predetermined one of the teeth 54 during assembly of the single use syringe to predetermine the dosage of the syringe. For brevity, the details of the function and interaction of the locking element 60 and the teeth 54 that are the same as those previously described will largely be omitted.

Figure 11:
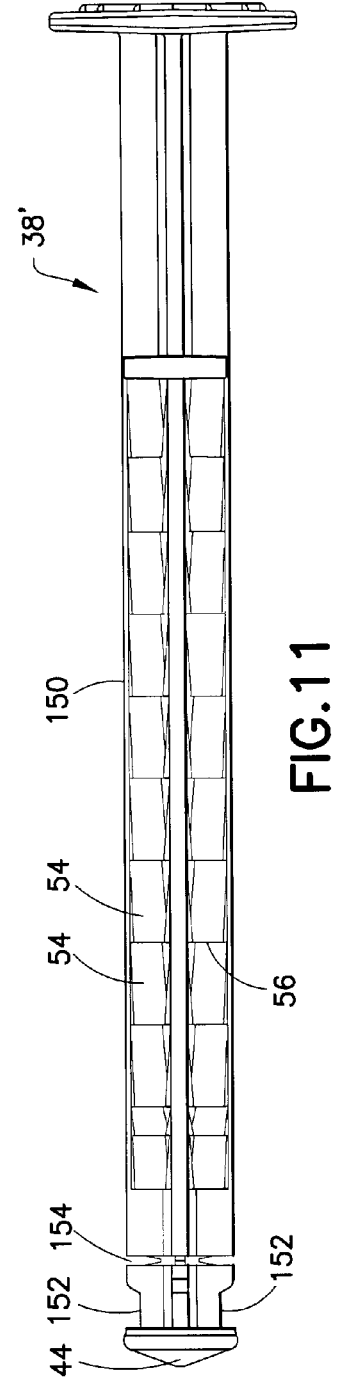
FIG. 11 depicts another single-use syringe embodiment with a breakable section distally disposed on the plunger rod.

In the exemplary embodiment of the present invention shown in FIG. 11, the cruciform plunger rod 38' has a larger cross-sectional diameter portion 150 and a reduced cross-sectional diameter portion 152. The reduced diameter portion 152 is disposed at the distal end of the plunger rod, adjacent to the plunger head or stopper 44. A breakable section 154 of reduced cross-sectional area is disposed between the distal-most teeth 54 and the plunger head or stopper 44, along the larger diameter portion 150 of the plunger rod. According to the exemplary embodiment shown in FIGS. 11 and 12*a*-12*b*, each of the radially extending walls of the cruciform plunger rod includes a breakable section 154, and the breakable sections 154 are longitudinally co-located on the plunger rod. The reduced cross-sectional area 154 weakens the plunger rod, preferably causing its destruction if an excessive rotational or axial force is applied to the plunger rod in an attempt to re-use the syringe, thus preventing its re-use.

Due to the improved positioning of the breakable section 154 along the plunger rod 38', when plunger rod 38' is withdrawn from the barrel for preparing an intended dosage, surfaces of the larger diameter portion 150, both proximal and distal with respect to the breakable section 154, remain in sliding contact with the exemplary barrel 22'. Such positioning of the breakable section 154 along the larger diameter portion 150 (as opposed to the reduced diameter portion 152) provides increased stability during normal use of the syringe. In other words, the breakable section 154 remains captured within the barrel 22' and supported by the inner wall 24 of the barrel even when plunger rod 38' is withdrawn from the barrel for maximal dosage. Additionally, this support and stability may improve a user's tactile experience of the syringe.

In addition, the breakable section 154 is provided along the plunger rod 38' such that the breakable section 154 is within the longitudinal length of the exemplary locking element 60' once the aspiration stroke of the plunger rod 38' for preparing the intended dosage is completed. In other words, when the plunger rod is withdrawn to prepare the intended dosage, such that the plunger head or stopper 44 abuts the distal edge of the locking element 60', the locking element 60' is disposed between with the shoulders 56 of the distal-most teeth 54 and the plunger head or stopper 44. Therefore (as shown, e.g., in FIG. 13), because the breakable section 154 is disposed between the teeth 54 and the stopper 44, the breakable section 154 is said to be positioned within the longitudinal length of the locking element 60'. Subsequently, as the exemplary plunger rod 38' is moved distally along with the locking element 60', the breakable section 154 remains positioned within the longitudinal length of the locking element 60'. This exemplary embodiment is advantageous over the prior art device for a number of reasons. First, the breakable section 154 does not interfere with the proximal longitudinal movement of the plunger rod with respect to the locking element 60' (i.e., during the aspiration stroke) or the conjoint distal longitudinal movement of the plunger rod and the locking element 60' (i.e., during the injection or dispensing stroke). As such, the breakable feature does not limit the range of desired dosage amounts to be administered by the exemplary device. Secondly, in this exemplary embodiment, the rear barbs 76' and 78' of the exemplary locking element 60', as shown in FIG. 7*b*, remain in a more proximal position with respect to the breakable section 154 throughout use of the syringe device. As discussed above, this is an important feature, such that the plunger rod is not susceptible to accidental failure. Any incidental rotational force or torque applied to the exemplary plunger rod during normal use will be translated to the locking element 60' at the point of engagement of the rear barbs 76' and 78' with the inner wall 24 of the exemplary barrel 22'. Therefore, the breakable section 154 will not be affected by such an incidental force and thus will not lead to accidental failure of the plunger rod and syringe device. The locking element 60' is rigid enough such any incidental rotational force is not capable of defeating the locking element 60'. However, as further discussed below, the application of excessive rotational force may be translated to the breakable section 154 causing destruction of the exemplary plunger rod.

Figure 12A:
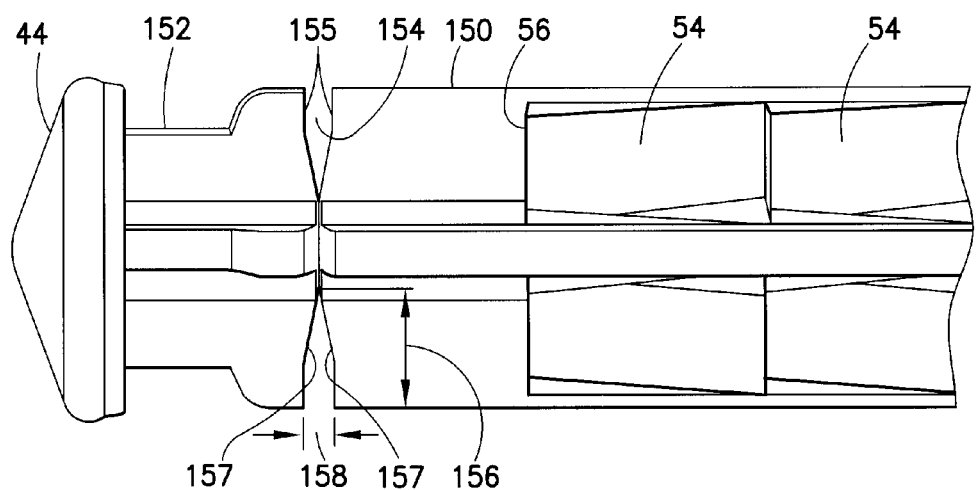
FIGS. 12a-12b depict an enlarged view of exemplary embodiments of the breakable section shown in FIG. 11.
Figure 12B:
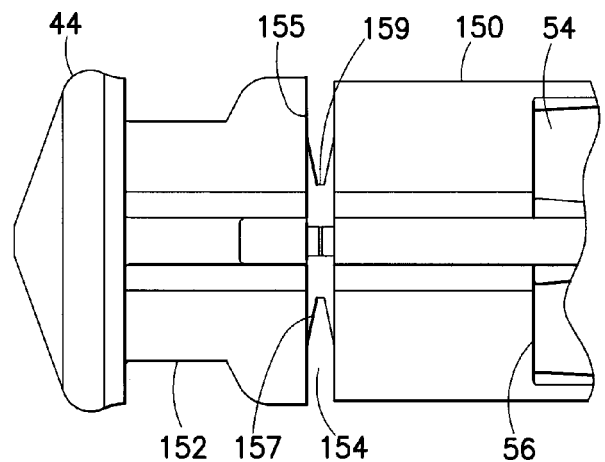

As shown, e.g., in FIG. 12*a*, the breakable section (or notch) 154 preferably includes a hybrid 'V' shaped gap or notch, the boundaries of which have a straight portion and a slanted portion. The straight portion includes a pair of straight, substantially parallel walls 155 that extend inwardly from an external radial diameter of the cruciform plunger rod. The straight walls 155 extend substantially perpendicular to a longitudinal axis of the plunger rod. The slanted portion includes a pair of slanted walls 157 extending toward each other from radially inward ends of the respective straight portions. In other words, the hybrid 'V' shaped gap or notch comprises portions that extend radially outward at an angle with respect to the longitudinal axis of the plunger rod and also portions that extend in a direction perpendicular therewith. The breakable section preferably begins on the edge of a longitudinal vane 52 or 104 and extends radially inward toward the cruciform intersection. It is preferable that a similar breakable section be formed on each of the remaining longitudinal vanes at a corresponding longitudinal position along the external radial edges of the plurality of vanes forming the cruciform plunger rod. In the embodiment of FIG. 12*a*, the slanted portions 157 contact each other at a minimum cross-sectional diameter of the plunger rod. In an alternate embodiment, as shown in FIG. 12*b*, the slanted portions 157 do not intersect. Instead, each is preferably joined by an edge parallel to the longitudinal axis of the plunger rod, forming a truncated 'V'. This embodiment is not only easier to manufacture, thus reducing manufacturing cost, but also results in a slightly more rigid plunger rod.

The slanted walls 157 in the embodiment of FIG. 12*a* converge to a point to concentrate stress and promote breakage. Thus, a radial depth 156 of the breakable section 154 with respect to the external radial diameter of the cruciform plunger rod is provided such that the plunger rod is designed to break when a predetermined tension force is applied to the plunger rod. In other words, the reduced cross-sectional area of the plunger at the breakable section 154 is designed to break at the predetermined tension. In other words, the plunger rod is "tuned" to break at a predetermined tension. The predetermined tension is ideally less than a force sufficient to defeat the locking element 60' or otherwise enable re-use of the syringe device. According to one embodiment, the depth 156 is designed to break the plunger rod with application of approximately 30 N (~6-7 lb) of tension. In this embodiment the depth 156 is preferably about 1.60 mm when the radial diameter of the plunger rod is about 4.6 mm.

Similarly, the radial depth of the breakable section 154 (and therefore the reduced cross-sectional area of the plunger) is also designed to break if a predetermined torsional force is applied to the plunger rod. In the above embodiment, the radial depth of the breakable section 154 would preferably be about 1.6 mm. According to one embodiment, the depth 156 is designed to break the rod within one rotation of the portion of the plunger rod proximal to the breakable section 154 with respect to the portion of the plunger rod distal to the breakable section 154. Notably, the permitted rotation of the plunger rod is not sufficient to defeat the locking element 60'. As such, the breakable section 154 is designed such that the plunger rod will be destroyed upon a predetermined rotational or axial force, the predetermined force being less than a required force to defeat the locking element 60' or otherwise enable re-use of the exemplary syringe assembly.

Additionally, because of the configuration of the two portions of the breakable section 154, a longitudinal width 158 of the breakable section (the distance between the pair of straight walls) is reduced in comparison to a simple V-notch. This configuration provides increased stability of the plunger rod during distal movement of the plunger rod upon injection or assembly. For example, during assembly of the syringe, when the plunger rod is inserted in the barrel, because the longitudinal width 158 is reduced in comparison with a simple V-notch, for a given rate of insertion, the amount of time that the larger diameter portion 150 of the plunger distal to the breakable section 154 is inserted prior to insertion of the larger diameter portion 150 proximal to the breakable section 154 is reduced. In other words, in combination with the aforementioned positioning of the breakable section 154, the reduction of the gap between edges of the breakable section increases torsional rigidity of the plunger rod, which is helpful during assembly. Thus, the plunger rod is less prone to undesired deflection (e.g., buckling), and is therefore more stable during insertion into the barrel.

Further, the longitudinal width 158 of the breakable section 154 is preferably sized so that the straight walls do not contact each other during normal compression of the plunger rod according to the intended use of the syringe assembly.

Further still, reduction of the longitudinal width 158 of the breakable section may be advantageous during a manufacturing molding process. In such a process, ejector pins may be located proximal to the breakable section 154, thereby preventing premature bending and/or breakage.

Figure 13:
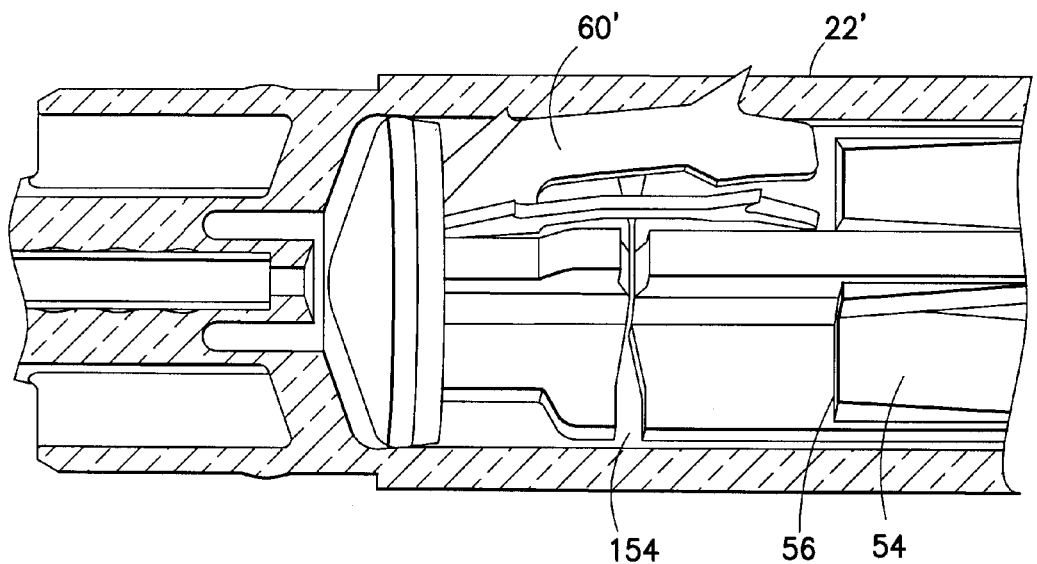
FIGS. 13 and 14 depict views of the functionality of the breakable section shown in FIG. 11.
Figure 14:
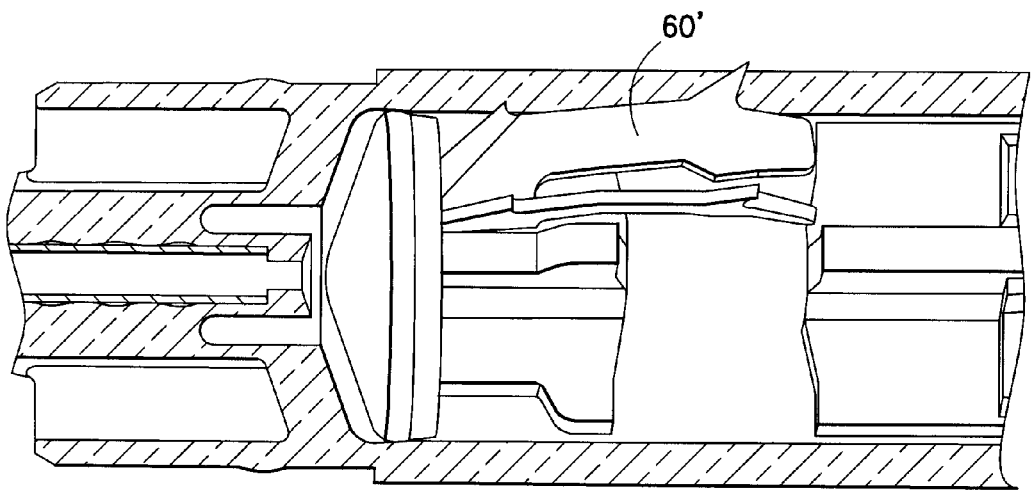

FIGS. 13 and 14 illustrate the breaking operation of the exemplary plunger rod described above with respect to FIGS. 11 and 12*a*-12*b*. In FIG. 13 the plunger rod 38' has been distally translated during the injection stroke, and has been slightly proximally translated, such that the exemplary locking element 60' is engaged with the stopper 44 and the proximal barbs 76' and 78' of the locking element 60' are engaged with the internal surface of the barrel 22'. Subsequent to the state illustrated in FIG. 13, because the locking element 60' resists further proximal translation of the plunger rod, any axial force is concentrated at the reduced cross-section of the breakable section 154. Once an excessive predetermined tensional and/or torsional force is applied to the plunger rod, the plunger rod breaks at the breakable section 154, as illustrated in FIG. 14.

According to one embodiment, the breakable section 154 is designed to break in tension and torsion prior to the disabling of the stopper by the optional cutting edge (e.g., 88) of the locking element 60'. Additionally, according to the preferred embodiments, the force required to break (separate) the plunger rod at the breakable section 154, is higher than the forces required to use the syringe under normal operating conditions and lower than any force required to disengage the locking element 60 or otherwise attempt the re-use the syringe assembly.

One possible technique that may be employed to intentionally misuse the syringe assembly of the prior art device requires the user to withdraw the plunger rod only a minimal distance such that the proximal legs 70 and 72 of the locking element 60 do not ride over the shoulders 56 of the teeth 54 which are engaging the proximal legs 70 and 72. This minimal distance is necessarily determined by the length of the teeth 54 along the plunger rod. If the plunger rod can be extracted such a minimal distance, the locking element will not be forced distally during injection due to the non-engagement of the proximal legs of the locking element with a subsequent shoulder 56 of an adjacent tooth 54. A user may then potentially re-use the syringe device indefinitely, albeit only to administer the reduced volume determined by the distance of retraction of the plunger rod. Due to the increased barrel diameter of the prior art device, such a reduced volume may be large enough to encourage such intentional misuse of the syringe assembly. However, due to the reduced diameter of the exemplary barrel 22', and thus a reduced volume with respect to a length of the aspiration stroke, the potential for indefinite re-use is less of a concern. Nevertheless, an exemplary embodiment of the present invention includes an additional feature to prevent such intentional misuse.

FIGS. 15-18 show several exemplary embodiments for preventing the indefinite misuse of the prior art syringe device described above. Specifically, FIGS. 15a and 15b depict one exemplary embodiment of providing intermediate teeth 254 with distal facing shoulders 256, preferably of the same height as shoulder 56 of teeth 54. The intermediate teeth 254 are provided in substantially the same way and perform similar functionality as that of teeth 54 discussed throughout. The intermediate shoulder 256 is preferably provided between the two most distal facing shoulders 56 of exemplary embodiments of the present invention. As can best be seen in FIG. 15b, the intermediate tooth 254 in an exemplary embodiment is provided atop the distal most tooth 54, in a "piggy-back" fashion. In an alternate embodiment, however, the intermediate tooth 254 can be provided as a separate tooth positioned between the two most distal teeth 54. As such, the plunger rod 38' would essentially comprise two distinct teeth of equal height, but not necessarily equal length. The longitudinal length of the exemplary intermediate tooth 254 is determined by a balance between a desired angle of the tooth 254 as well as a desired height of the shoulder 256. Locking element 60' sits atop of the teeth 54 and 254 during normal use of the syringe assembly. Thus, as the height of the shoulder 56 and 256 increases, the injection and aspiration forces also increase since the barbs 84' and 86' of locking element 60' are urged into engagement with the inner surface of the barrel 22'. Further, the angle of the teeth must be considered for providing a sufficient edge of the shoulder 256 for engagement with proximal legs 70' and 72' of locking element 60' while maintaining acceptable injection and aspiration forces resulting from the flexibility of locking element 60'. FIG. 15b depicts a specific relationship of the longitudinal length of the intermediate tooth with respect to tooth 54; however, such a relationship is not required. Any such length and height of intermediate step 254 can be chosen, as long as the syringe assembly maintains the intended functionality.

Figure 15A:
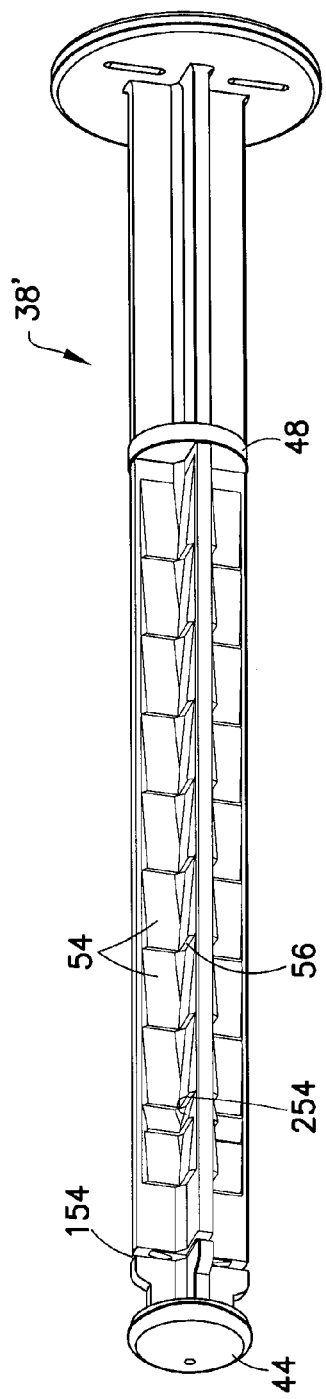
FIGS. 15a and 15b depict another single use syringe embodiment with an intermediate tooth provided on the distal most tooth of the plunger rod shown in FIG. 9.
Figure 15B:
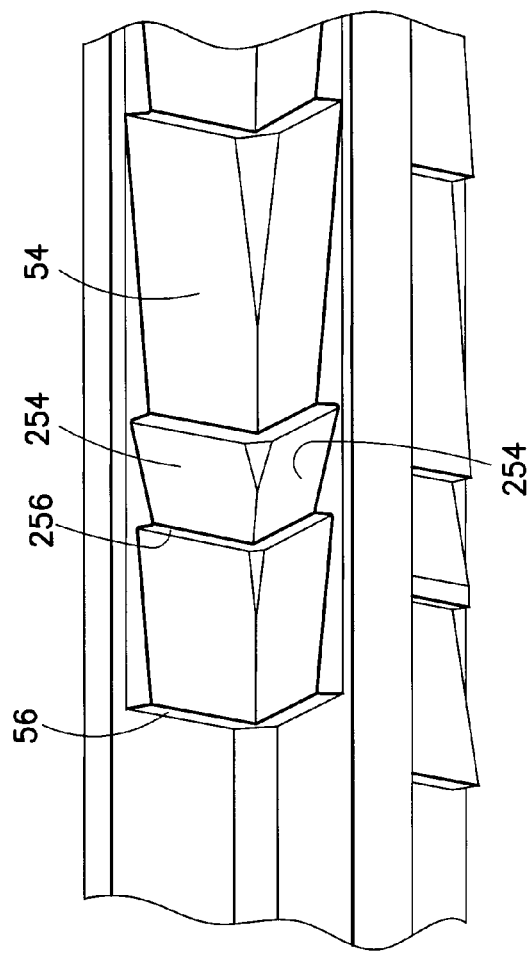
Figure 15C:
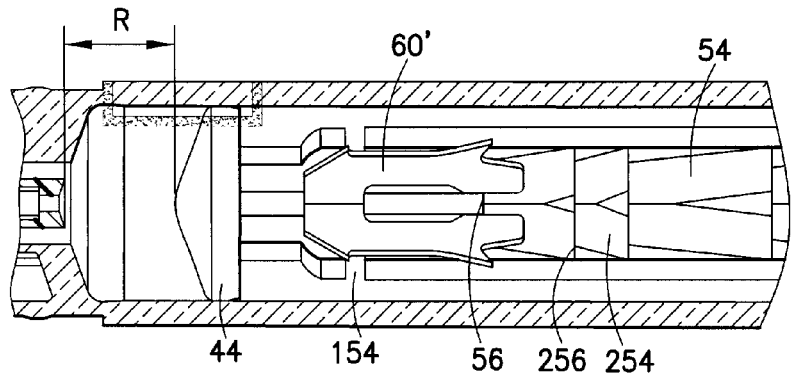
FIGS. 15c-15f depict views of the functionality of the intermediate tooth shown in FIGS. 15a and 15b.
Figure 15D:
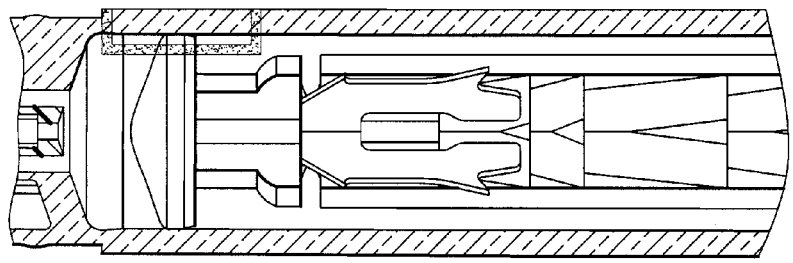
Figure 15E:
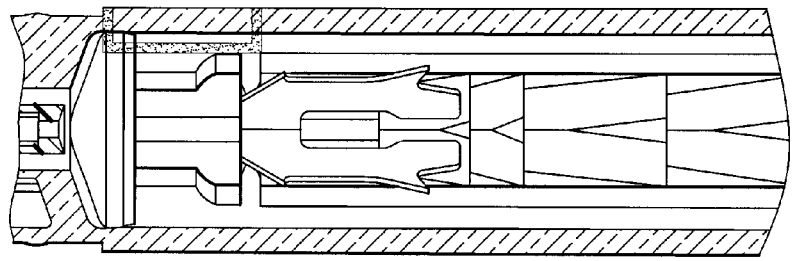
Figure 15F:
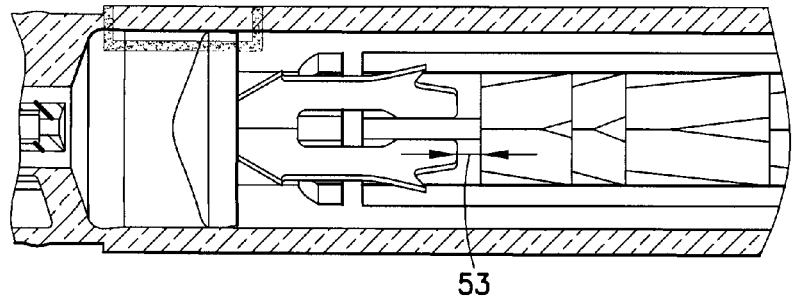

Functionality of the intermediate tooth 254 and shoulder 256 will be discussed with respect to FIGS. 15c-15f. FIG. 15c depicts an exemplary locking element 60' pre-set at a position along plunger rod 38' for the administration of a 0.05 ml dose. The plunger rod 38' is retracted a length R. As shown, the length R is less than the length required for setting the intended dose. Length R is carefully manipulated by the user such that the proximal edge of legs 70' and 72' of the exemplary locking element 60' do not ride over the distal most shoulder 56. As such, during administration of this reduced dosage it is the shoulder 256 of the intermediate tooth that drives the locking element in the distal direction. Because of the more proximal distal placement of the intermediate shoulder 256, the locking element 60' is driven a greater distance distally, as shown in FIG. 15e, than it would have in the absence of the intermediate tooth 254. As such, a user of the prior art syringe device would have been able to administer the reduced dosage determined by length R an indefinite number of times. However, because of the placement of intermediate tooth 254, upon subsequent aspiration of the plunger rod 38', in order to realize a potentially usable dosage, the user must retract the plunger rod a distance similar to that of R. Yet, due to the distal advancement of the locking element 60' discussed above, at this distance of retraction, the proximal legs 70' and 72' now ride over the distal most shoulder 56, as shown in FIG. 15f. Therefore, upon subsequent injection, the locking element 60' will be driven to the distal most end of the syringe barrel 22', as can be appreciated in view of FIG. 15f, rendering the syringe assembly unusable.

The embodiment of FIGS. 15a-15f depict an intermediate tooth 254 provided only between the two most distal shoulders 56 of the plunger rod 38'. This is so, because it is as the locking element nears the distal most end of the barrel that intentional misuse of the syringe assembly is most likely to occur. Namely, after a user administers a first large dose, less than the maximum dose, that the user may potentially attempt to re-use the syringe assembly. Thus, it is after such a first dose, that the locking element is likely positioned near the distal end of the barrel. Further, when the intended dose is set at 0.05 ml, the locking element is already positioned near the distal end. Thus the exemplary feature is especially useful when the intended dose is 0.05 ml. In another exemplary embodiment, it may be desired to provide the intermediate teeth 254 between the teeth 54 along substantially the entire usable length of an exemplary plunger rod. For instance, the plunger rod will comprise alternating teeth 54 and 254 along substantially the entire usable length thereof. It is preferred that the height of the shoulders 56 and 256 are equal, but the length of the teeth 254 can be chosen for desired functionality.

Figure 16A:
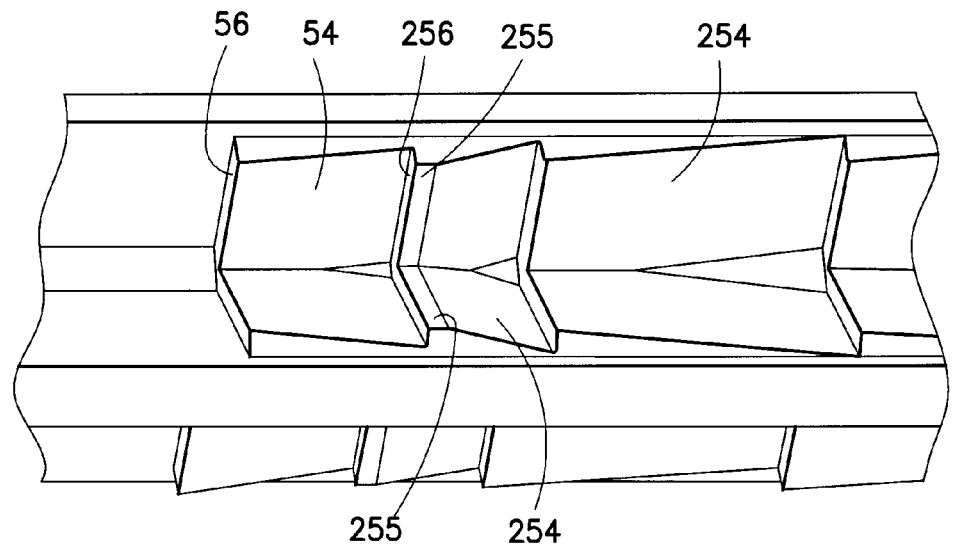
FIGS. 16a-18 depict alternative embodiments of an intermediate tooth or surface for use in exemplary embodiments of the present invention.
Figure 16B:
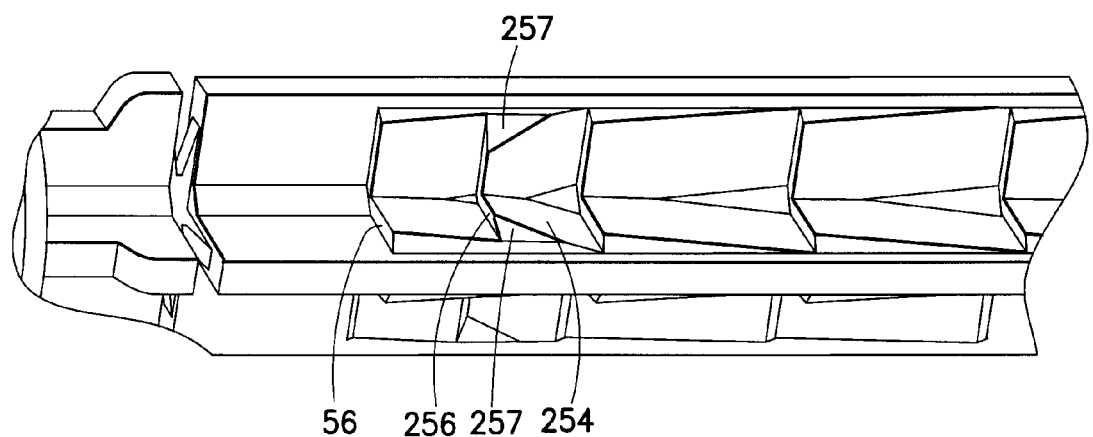

FIG. 16a depicts an alternate embodiment of the intermediate tooth 254. In this embodiment, a desired angle of tooth 254 can be utilized without compromising the desired length of tooth 254 or the height of shoulder 256. Thus the intermediate tooth includes a flattened surface 255 near the distal end of the tooth at the desired height of shoulder 256. The length of the flattened surface is then determined by the desired length of the intermediate tooth 254. FIG. 16b depicts another exemplary embodiment of an intermediate tooth 254. In this embodiment, intermediate tooth 254 includes an angled surface 257 provided along the radially outer edge of the intermediate tooth 254 adjoining shoulder 256. Such an angled surface 257 is provided to reduce the injection and aspiration forces associated with providing an additional shoulder for the locking element 60' to ride over. The angled surface 257 is provided on the tooth 254 surface where the proximal legs 70' and 72' of an exemplary locking element 60' primarily slidably engage the tooth 254. The above exemplary embodiments of intermediate teeth 254 can also be utilized in similar embodiments as those described above with respect to FIGS. 15a and 15b, and are not limited by the specific embodiment shown in FIGS. 16 and 16b.

Figure 17A:
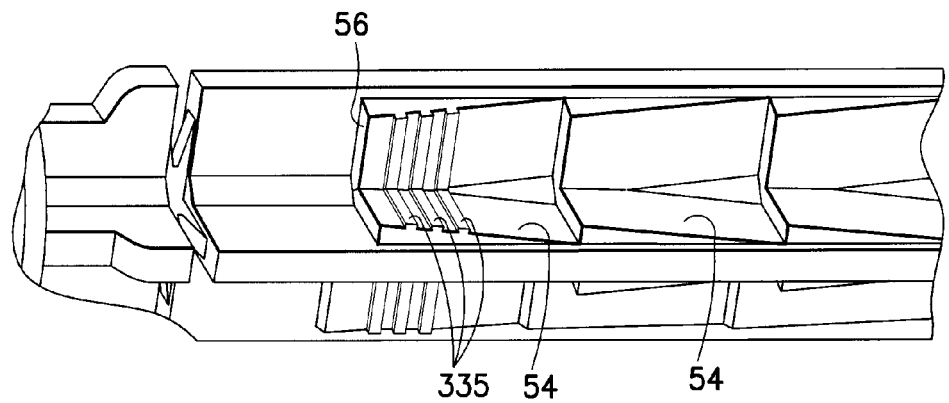
Figure 17B:
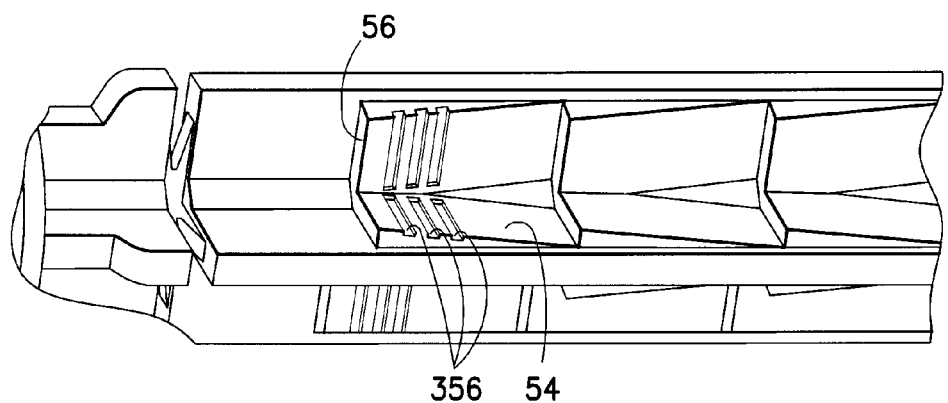

FIGS. 17a and 17b depict additional embodiments for preventing the indefinite reuse of an exemplary syringe assembly described above, without the aid of the additional intermediate tooth 254. As shown in FIG. 17a, a plurality of intermediate steps 355 are preferably provided along the angled surface of the distal most teeth 54. The height, number and spacing of the steps 355 may be chosen to provide optimal functionality of the syringe assembly. Step 355 performs a similar function as the shoulders 56 and 256 in exemplary embodiments of the present invention. Namely, the step serves as an edge to drive an exemplary locking element 60' in the distal direction upon engagement of the intermediate step. In one exemplary embodiment, as shown in FIG. 17b, intermediate indentations 356, may preferably be provided to perform the same function as steps 355.

Figure 18:
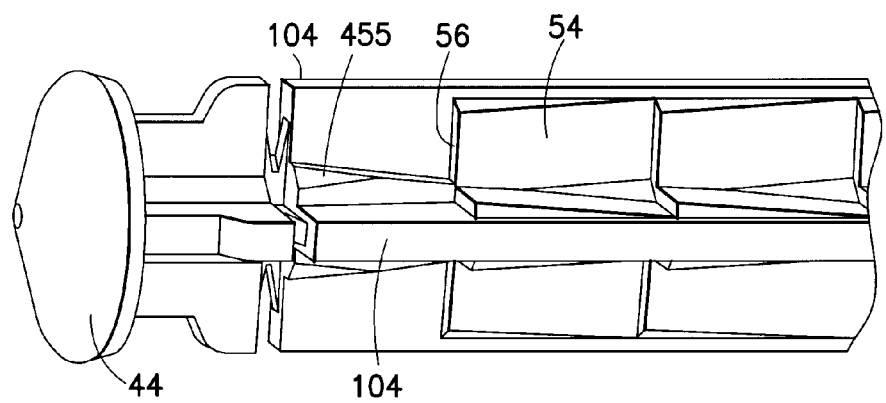

FIG. 18 depicts yet another exemplary embodiment that provides a slender surface 455 that juts radially outward from the intersection of longitudinal vanes 104 located in the recess provided between the distal most step 54 and the breakable section 154. The exemplary slender surface 455 is sized and positioned such that as the plunger rod 38' is retracted a predetermined distance in the proximal direction, the proximal edge of bridge section 75 of an exemplary locking element 60' slides over and engages the distal edge of the surface 455. This engagement functions to drive the locking element 60' in the distal direction upon an injection stroke of the plunger rod 38'. As such, the engagement of the bridge section 75 with the surface 455 functions similarly to that of the engagement between the proximal legs 70' and 72' with shoulders 56.

Figure 19A:
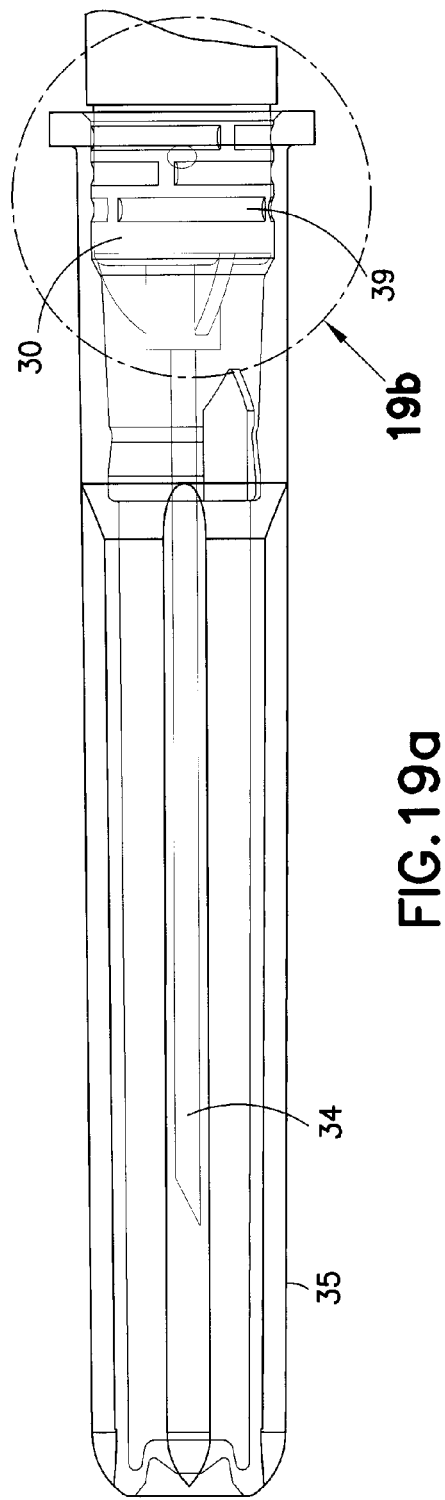
FIGS. 19a and 19b depict an exemplary embodiment of a needle safety shield for use in exemplary embodiments of the present invention.
Figure 19B:
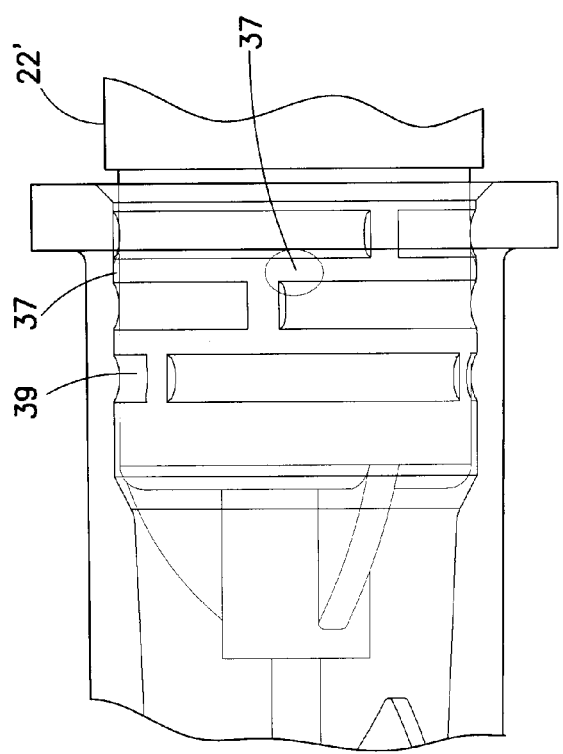

In an exemplary embodiment of the present invention, the syringe assembly shown in FIG. 3 further utilizes an improved needle shield 35, as shown in FIGS. 19a and 19b. The improved needle shield includes a plurality of ridges 39 provided on an inner surface of the shield that engages the distal end 30 of the syringe barrel. The space between the ridges effectively form a space or recess for accommodating a positive feature 37 protruding from the outer surface of the distal end 30 of the barrel. The positive feature 37 can be seen in FIGS. 3 and 19b. The positive feature 37 is formed as a half spherical node or bump with a smooth surface for sliding into and out of the recess provided on the exemplary needle shield 35 upon reasonable force applied by the user. Further, the engagement of the positive feature 37 and the ridges 39 provides an audible and tactile indication, thus indicating to the user that the needle shield 35 is properly attached.

The syringe barrel 22' in exemplary embodiments of the present invention may be constructed of a wide variety of thermoplastic materials such as polypropylene, polyethylene and combinations thereof. In an exemplary embodiment of the present invention, accurate dose setting can be facilitated by the use of materials providing clear visibility, and the use of fixed-dose and bold single scale markings on one or more surfaces of the device. Similarly, thermoplastic materials such as polypropylene, polyethylene and polystyrene are preferred for the plunger rod and integral plunger head or stopper. A wide variety of materials such as natural rubber, synthetic rubber and thermoplastic elastomers are suitable for the plunger head or stopper if the plunger head or stopper is manufactured as a separate component or made by a two-shot molding process or the like. The choice of plunger head or stopper material will depend on compatibility with the medication being used and the barrel material and thickness since the plunger head or stopper must form a seal with the inside surface of the barrel to deliver medication through the needle cannula. In an exemplary embodiment, the diameter of the plunger head is preferably about 4.83 mm, so as to provide a suitable seal while optimizing the aspiration and injection forces required during normal use. Further, the plunger head, plunger rod, and/or barrel can be constructed of a colored or tinted material, or have an applied color, to indicate one or more features of the device, such as needle gauge or an intended dose. For example, the device can comprise an ISO color-coded plunger rod to facilitate quick identification of the needle gauge.

As previously described, it is preferable that the locking element be fabricated from a material which is harder than the barrel so that the locking barbs may effectively engage the barrel. Resilient spring-like properties are also desirable along with low cost and dimensionally consistent fabrication. With this in mind, sheet metal is a desirable material for the locking element, with stainless steel being preferred. Although the locking element of the preferred embodiment is fabricated from a single sheet, it is within the purview of the instant invention to include locking elements made of other forms and/or containing multiple parts. Locking elements having structures other than that shown and described herein could also be successfully employed. Alternatively, one or more distally extending barbs could be provided at the distal end of the locking element for rendering the plunger head or stopper unusable.

The syringe barrel employed in accordance with the invention may have a varying wall thickness along its length. The portion of the barrel used for containing medication could be relatively thin and resilient to ensure proper sealing with the plunger head or stopper. The remainder of the barrel could be relatively thick and non-resilient such that it would tend to crack if squeezed by pliers or another device used for attempted tampering. Sufficient barrel crystallinity is desirable in the area of the locking element to cause this area to crack upon deformation of the syringe barrel to an extent that would permit retraction of the plunger rod assembly with the locking element.

The embodiments of the present invention provide a plunger rod that automatically locks after injection, thereby preventing the syringe from being reused. That is, the passive auto-disable technology described above ensures that at least the plunger rod is automatically locked after injection, preventing the syringe from being reused. Thus, it can be seen that embodiments of the present invention can provide a simple, reliable, easily fabricated, single-use syringe which becomes inoperable or incapable of further use without any additional act on the part of the user, and which allows the plunger rod to break if excessive force is applied in an attempt to re-use the syringe.

Further, embodiments of the present invention can provide a small, or mini-device, suitable for use with children, infants or other pediatric uses, which significantly relieves patient anxiety upon seeing the device. The exemplary embodiments of the present invention provide a smaller device that avoids the levels of patient anxiety associated with seeing a larger device, especially with pediatric patients, while still including passive auto-disable technology. Still further, exemplary embodiments of the present invention provide a smaller device that is more suitable for the typical size of an immunization dosage. Such immunization, vaccine, and other similar dosage amounts are often very small, and the use of exemplary embodiments of the present invention result in many benefits, such as less waste of dosage contents and reduced cost. Further, the exemplary smaller size of the device has been shown to be preferred by healthcare workers over a larger-size syringe, and allows healthcare workers to maintain their standard injection techniques. In doing so, exemplary embodiments of the present invention provide a next generation of immunization syringes.

While the present invention has been shown and described with reference to particular illustrative embodiments, it is not to be restricted by such exemplary embodiments. It is to be appreciated that those skilled in the art can change or modify the exemplary embodiments without departing from and the scope and spirit of the present invention as defined in the appended claims and their equivalents.

What is claimed is:

1. A method of operating a syringe, the syringe comprising a barrel, a locking element, and a plunger rod assembly including a stopper, a user interface flange, an elongate body portion, a recess disposed along the elongate body portion, and a plurality of first teeth defining a plurality of distally facing shoulders, the locking element being positionable within the recess, the plunger rod assembly and the locking element being inserted into the barrel, the locking element being prevented from displacing proximally relative to the barrel, the method comprising:

proximally displacing the plunger rod assembly relative to the barrel to draw fluid into the barrel, while the locking element remains substantially stationary relative to the barrel;

engaging a proximal end of the locking element with the most distal of the distally facing shoulders, wherein the elongate body portion extends from the stopper to the flange, and the distally facing shoulders are substantially equally spaced along a majority of the elongate body portion; and distally displacing both the plunger rod assembly and the locking element to dispense the fluid from the barrel, wherein the locking element prevents re-use of the syringe.

2. The method according to claim 1, wherein subsequent proximal displacement of the plunger rod assembly is prevented due to engagement of the plunger rod assembly with the locking element.

3. The method according to claim 1, further comprising performing a vein check by proximally displacing the plunger rod assembly subsequent to inserting a cannula connected to the barrel into a patient's skin to detect an inflow of blood into the distal end of the syringe, wherein a distance between the stopper and the most distal of the of the distally facing shoulders is greater than a longitudinal length of the locking element.

4. The method according to claim 1, wherein the method is carried out using a locking element comprising:
   a generally V-shaped body portion including first and second radially extending walls joined along a longitudinal axis;
   first and second legs respectively extending in a proximal direction from the first and second walls, each of the legs including a proximal end portion engageable with the distally facing shoulders of the plunger rod assembly of the syringe, each proximal end portion including an outer edge having a barb portion angled radially outward for engaging an internal surface of the syringe barrel, and an end portion angled radially inward; and
   a distal end portion integral with the generally V-shaped body portion, the distal end portion including at least one distal edge portion extending substantially perpendicular to the longitudinal axis from the vertex of the V-shaped body portion, the distal edge portion having a length less than a distance between the vertex and the outer edge of the first leg.

5. A method of manufacturing a syringe, comprising:
   positioning a locking element within a recess of a plunger rod assembly, the plunger rod assembly including a stopper, a user interface flange, an elongate body portion extending from the stopper to the flange, and a plurality of first teeth defining a plurality of distally facing shoulders that are substantially equally spaced along a majority of the elongate body portion, the recess being disposed along the elongate body portion; and
   inserting the plunger rod assembly and the locking element into a syringe barrel;
   wherein the locking element is substantially prevented from displacing proximally relative to the barrel.

6. The method according to claim 5, further comprising determining a maximum desired dosage, wherein positioning the locking element longitudinally along the recess comprises setting a maximum dosage volume for the syringe.

7. The method according to claim 5, further comprising providing a reduced cross-sectional area on the elongate portion of the plunger rod assembly configured to break upon the application of axial or torsional force to the plunger rod assembly above a predetermined limit.

8. The method according to claim 7, wherein the locking element includes a body portion having a proximal end that engages the plunger rod assembly and an inner surface of the barrel at a surface more proximal than the reduced cross-sectional area.

9. The method according to claim 7, wherein the reduced cross-sectional area is provided within a distal end of the elongate body portion of the plunger rod assembly, the distal end comprising a portion extending proximally from the stopper to the most distal of the distally facing shoulders.

10. The method according to claim 7, further comprising providing a plurality of reduced cross-sectional areas along a majority of the elongate body portion of the plunger rod assembly.

11. The method according to claim 7, further comprising providing a plurality of longitudinal vanes on the elongate body portion of the plunger rod assembly to define the recess, wherein the reduced cross-sectional area is defined by a notch extending radially inward from an external edge provided at a corresponding position on each of the longitudinal vanes.

12. The method according to claim 7, further comprising providing a plurality of longitudinal vanes on the elongate body portion of the plunger rod assembly to define the recess, wherein the reduced cross-sectional area is defined by a hole provided at a corresponding position on each of the longitudinal vanes.

13. The method according to claim 5, further comprising:
   on a distal-most first tooth of the plurality of first teeth formed on the elongate body portion, providing an angled surface extending proximally from a top of the distally facing shoulder to a base of an adjacent distally facing shoulder; and
   providing at least one raised step on the angled surface.

14. The method according to claim 5, further comprising:
   on a distal-most first tooth of the plurality of first teeth formed on the elongate body portion, providing an angled surface extending proximally from a top of the distally facing shoulder to a base of an adjacent distally facing shoulder; and
   providing at least one indentation on the angled surface.

15. A method of operating a syringe, the syringe comprising a barrel, a locking element, and a plunger rod assembly including an elongate body portion, a recess disposed along the elongate body portion, a plurality of first teeth defining a plurality of distally facing shoulders, and a portion of reduced cross-sectional area configured to break upon the application of axial or torsional force to the plunger rod assembly above a predetermined limit, the plunger rod assembly and the locking element being inserted into the barrel, the locking element being prevented from displacing proximally relative to the barrel, the method comprising:
   proximally displacing the plunger rod assembly relative to the barrel to draw fluid into the barrel, while the locking element remains substantially stationary relative to the barrel;
   engaging a proximal end of the locking element with the most distal of the distally facing shoulders of the plurality of first teeth, the plurality of first teeth being disposed within the recess, the distally facing shoulders being substantially equally spaced along a majority of the elongate body portion; and
   distally displacing both the plunger rod assembly and the locking element to dispense the fluid from the barrel.

16. The method according to claim 15, wherein subsequent proximal displacement of the plunger rod assembly is prevented due to the reduced cross-sectional area and engagement of the plunger rod assembly with the locking element.

17. The method according to claim 15, further comprising performing a vein check by proximally displacing the plunger rod assembly subsequent to inserting a cannula connected to the barrel into a patient's skin to detect an inflow of blood into the distal end of the syringe, wherein a distance between the stopper and the most distal of the of the distally facing shoulders is greater than a longitudinal length of the locking element.

18. A method of manufacturing a syringe, comprising:
positioning a locking element within a recess of a plunger rod assembly, the plunger rod assembly including an elongate body portion, a recess along the elongate body portion, a plurality of first teeth within the recess defining a plurality of distally facing shoulders that are substantially equally spaced along a majority of the elongate body portion, and a portion of reduced cross-sectional area configured to break upon the application of axial or torsional force to the plunger rod assembly above a predetermined limit; and
inserting the plunger rod assembly and the locking element into a syringe barrel;
wherein the locking element is substantially prevented from displacing proximally relative to the barrel.

19. The method according to claim 18, further comprising determining a maximum desired dosage, wherein positioning the locking element longitudinally along the recess comprises setting a maximum dosage volume for the syringe.

20. The method according to claim 18, wherein the locking element includes a body portion having a proximal end that engages the plunger rod assembly and an inner surface of the barrel at a surface more proximal than the reduced cross-sectional area.

21. The method according to claim 18, wherein the reduced cross-sectional area is provided within a distal end of the elongate body portion of the plunger rod assembly, the distal end comprising a portion extending proximally from the stopper to the most distal of the distally facing shoulders.

22. The method according to claim 18, further comprising providing a plurality of reduced cross-sectional areas along a majority of the elongate body portion of the plunger rod assembly.

23. The method according to claim 18, further comprising providing a plurality of longitudinal vanes on the elongate body portion of the plunger rod assembly to define the recess, wherein the reduced cross-sectional area is defined by a notch extending radially inward from an external edge provided at a corresponding position on each of the longitudinal vanes.

24. The method according to claim 18, further comprising providing a plurality of longitudinal vanes on the elongate body portion of the plunger rod assembly to define the recess, wherein the reduced cross-sectional area is defined by a hole provided at a corresponding position on each of the longitudinal vanes.

25. The method according to claim 18, further comprising:
on a distal-most first tooth of the plurality of first teeth formed on the elongate body portion, providing an angled surface extending proximally from a top of the distally facing shoulder to a base of an adjacent distally facing shoulder; and
providing at least one raised step on the angled surface.

26. The method according to claim 18, further comprising:
on a distal-most first tooth of the plurality of first teeth formed on the elongate body portion, providing an angled surface extending proximally from a top of the distally facing shoulder to a base of an adjacent distally facing shoulder; and
providing at least one indentation on the angled surface.

27. A locking element for a syringe, for preventing reuse of the syringe, the locking element comprising:
a generally V-shaped body portion including first and second radially extending walls joined along a longitudinal axis;
first and second legs respectively extending in a proximal direction from the first and second walls, each of the legs including a proximal end portion engageable with a distally facing shoulder of a plunger rod assembly of the syringe, each proximal end portion including an outer edge having a barb portion angled radially outward for engaging an internal surface of a syringe barrel, and an end portion angled radially inward, each end portion meeting a a proximal edge or surface of the locking element at a radius; and
a distal end portion integral with the generally V-shaped body portion, the distal end portion including at least one distal edge portion extending substantially perpendicular to the longitudinal axis from the vertex of the V-shaped body portion, the distal edge portion having a length less than a distance between the vertex and the outer edge of the first leg.

28. The locking element according to claim 27, wherein the distal edge portion is straight.

29. The locking element according to claim 27, wherein the distal end portion comprises a bridge portion connecting two distal edge portions, wherein a length of the bridge portion along the longitudinal axis is about 27% of the length of the locking element along the longitudinal axis.

30. A locking element for a syringe, for preventing reuse of the syringe, the locking element comprising:
a generally V-shaped body portion including first and second radially extending walls joined along a longitudinal axis;
first and second legs respectively extending in a proximal direction from the first and second walls, each of the legs including a proximal end portion engageable with a distally facing shoulder of a plunger rod assembly of the syringe, each proximal end portion including an outer edge having a barb portion angled radially outward for engaging an internal surface of a syringe barrel, and an end portion angled radially inward; and
a distal end portion integral with the generally V-shaped body portion, the distal end portion including at least one distal edge portion extending substantially perpendicular to the longitudinal axis from the vertex of the V-shaped body portion, the distal edge portion having a length less than a distance between the vertex and the outer edge of the first leg:
wherein the distal edge portion is sharpened.

\* \* \* \* \*